US011817233B2

(12) United States Patent
Watanabe

(10) Patent No.: US 11,817,233 B2
(45) Date of Patent: Nov. 14, 2023

(54) IMAGE PICKUP APPARATUS, ENDOSCOPE APPARATUS INCLUDING IMAGE PICKUP APPARATUS, MOBILE BODY INCLUDING IMAGE PICKUP APPARATUS, IMAGE PICKUP UNIT, AND VIDEO PROCESSING UNIT

(71) Applicant: OLYMPUS CORPORATION, Hachioji (JP)

(72) Inventor: Tadashi Watanabe, Nagano (JP)

(73) Assignee: OLYMPUS CORPORATION, Tokyo (JP)

(*) Notice: Subject to any disclaimer, the term of this patent is extended or adjusted under 35 U.S.C. 154(b) by 164 days.

(21) Appl. No.: 17/409,541

(22) Filed: Aug. 23, 2021

(65) Prior Publication Data

US 2022/0046205 A1 Feb. 10, 2022

Related U.S. Application Data

(63) Continuation of application No. PCT/JP2020/001018, filed on Jan. 15, 2020.

(30) Foreign Application Priority Data

Feb. 25, 2019 (JP) ................................ 2019-032059

(51) Int. Cl.
*H01B 1/22* (2006.01)
*H04N 7/045* (2006.01)
(Continued)

(52) U.S. Cl.
CPC ............... *H01B 1/22* (2013.01); *H04N 7/045* (2013.01); *H04N 23/55* (2023.01);
(Continued)

(58) Field of Classification Search
CPC .......... H01B 1/22; H04N 7/045; H04N 23/55; H04N 23/682; H04N 23/80; H04N 7/183;
(Continued)

(56) References Cited

U.S. PATENT DOCUMENTS 10,404,915 B1 * 9/2019 Chen .................... H04N 23/683
2002/0142653 A1 * 10/2002 Hosaka .................. H01R 4/024
439/578

(Continued)

FOREIGN PATENT DOCUMENTS

CN 105359421 A 2/2016
JP 2516140 B2 7/1996

(Continued)

OTHER PUBLICATIONS

International Search Report (ISR) (and English translation thereof) dated Apr. 14, 2020 issued in International Application No. PCT/JP2020/001018.

(Continued)

*Primary Examiner* — Michael E Teitelbaum
(74) *Attorney, Agent, or Firm* — Holtz, Holtz & Volek PC

(57) ABSTRACT

An image pickup apparatus includes, between a first unit including an image pickup device and a second unit including a video processing circuit, a waveguide path through which a millimeter wave or a submillimeter wave is transmitted, the second unit includes a millimeter-wave carrier-wave generation circuit and a demodulator configured to regenerate, from a millimeter-wave modulated wave generated by the first unit and received through the waveguide path, a video signal generated by the image pickup device, and the first unit includes a processing-transmission circuit configured to receive a millimeter-wave carrier wave through the waveguide path, generate a millimeter-wave modulated wave by superimposing the video signal gener- (Continued)

ated by the image pickup device on the millimeter-wave carrier wave, and transmit the millimeter-wave modulated wave toward the waveguide path.

13 Claims, 14 Drawing Sheets

(51) Int. Cl.

| | |
|---|---|
| ***H04N 23/55*** | (2023.01) |
| ***H04N 23/80*** | (2023.01) |
| ***H04N 23/68*** | (2023.01) |
| ***H04N 7/18*** | (2006.01) |
| ***H04N 23/56*** | (2023.01) |
| ***H04N 23/50*** | (2023.01) |

(52) U.S. Cl.
CPC ........... *H04N 23/682* (2023.01); *H04N 23/80* (2023.01); *H04N 7/183* (2013.01); *H04N 23/555* (2023.01); *H04N 23/56* (2023.01)

(58) Field of Classification Search
CPC .... H04N 23/555; H04N 23/56; H04N 23/687; H04N 7/20; H04N 23/65; H04N 23/663; A61B 1/00011; A61B 1/05; G02B 23/24; G03B 5/00; H01P 3/12; H01P 11/00
See application file for complete search history.

(56) References Cited

U.S. PATENT DOCUMENTS

2010/0091129 A1* 4/2010 Usuda .................... H04N 23/80 348/E7.003
2011/0037863 A1 2/2011 Mihota et al.
2011/0038282 A1* 2/2011 Mihota .................... H04B 3/52 455/500
2013/0050456 A1* 2/2013 Sakurai .................. H04N 23/74 348/311
2013/0328641 A1* 12/2013 Komori ..................... H01P 3/12 333/248
2014/0178064 A1* 6/2014 Hino ........................ H04B 3/52 398/41
2016/0373164 A1 12/2016 Kawasaki
2020/0060513 A1 2/2020 Ito et al.
2020/0091629 A1* 3/2020 Dove ...................... H01P 5/026
2021/0179112 A1* 6/2021 Tanimichi ........... B60W 40/105

FOREIGN PATENT DOCUMENTS

JP H11341337 A 12/1999
JP 2011039340 A 2/2011
JP 2014139692 A 7/2014
JP 2015019137 A 1/2015
JP 5725222 B2 5/2015
JP 2018191137 A 11/2018

OTHER PUBLICATIONS

Written Opinion dated Apr. 14, 2020 issued in International Application No. PCT/JP2020/001018.
Chinese Office Action dated Nov. 24, 2022, issued in counterpart Chinese Application No. 202080028665.7.
Japanese Office Action (and an English language translation thereof) dated Apr. 11, 2023, issued in counterpart Japanese Application No. 2019-032059.

* cited by examiner

IMAGE PICKUP APPARATUS, ENDOSCOPE APPARATUS INCLUDING IMAGE PICKUP APPARATUS, MOBILE BODY INCLUDING IMAGE PICKUP APPARATUS, IMAGE PICKUP UNIT, AND VIDEO PROCESSING UNIT

CROSS REFERENCE TO RELATED APPLICATION

This application is a continuation application of PCT/JP2020/001018 filed on Jan. 15, 2020 and claims benefit of Japanese Application No. 2019-032059 filed in Japan on Feb. 25, 2019, the entire contents of which are incorporated herein by this reference.

BACKGROUND OF THE INVENTION

1. Field of the Invention

The present invention relates to an image pickup apparatus, an endoscope apparatus including the image pickup apparatus, a mobile body including the image pickup apparatus, an image pickup unit, and a video processing unit, and particularly relates to an image pickup apparatus including a waveguide path through which electric wave transmission in a millimeter-wave or submillimeter-wave band or higher is performed, an endoscope apparatus including the image pickup apparatus, a mobile body including the image pickup apparatus, an image pickup unit, and a video processing unit.

2. Description of the Related Art

Recently, a communication environment having a communication speed exceeding 1 Gbps has become widely available to general households due to a technology such as what is called "Fiber To The Home" (FTTH). In addition, terminals having high processing performance, such as smartphones have proliferated, and available communication technologies and information processing speed, in other words, "hardware performance" has been significantly improved.

In addition, quality and amount of information available to individuals or to companies, in other words, "software use" has been significantly expanded due to use of high-definition and large-volume video such as 4K or 8K images exceeding what is called full high definition (FHD), increase of information access through the Internet, and the like.

In such a trend, demand for an image pickup apparatus for acquiring high-definition video of 4K or 8K has been increasing, but a volume of video information of the high-definition video is large due to increase of the number of pixels, and thus has become difficult to be handled by a conventional communication method. Specifically, even an information transmission speed exceeding 50 Gbps has been required to obtain a video having realistic sensation through 4K or 8K video transmission (for example, to increase an amount of luminance information or the number of frames per second).

Such an information transmission speed exceeding 50 Gbps exceeds limitations of a differential line using a metal wire, such as low voltage differential signaling (LVDS), which has been conventionally widely used.

Such a transmission speed can be handled by a method of transmission through a plurality of lines, but in this case, it is difficult to guarantee difference among signal timings of all lines, and a circuit for guaranteeing the difference has high technological difficulties and a large circuit scale, and thus general-purpose use of the circuit is difficult. Thus, it has a large number of difficulties in using, for communication in an order of several tens Gbps or higher, a conventional line using a metal wire, and is not realistic.

Optical communication technologies, which have been conventionally used in long-distance transmission or high-speed communication at a data center, can be used for communication in the order of several tens Gbps or higher as described above, but an optical communication line is typically rigid and less flexible, and furthermore, an optical-communication transmission-reception unit is extremely expensive and not appropriate as a communication means in a product in a popular price range.

In such a situation, development has been made on millimeter-wave communication employed as a wired communication means that achieves both high-speed communication in the order of several tens Gbps or higher and a moderate price. For example, Japanese Patent Application Laid-Open Publication No. 2011-39340 discloses an image pickup device configured to perform high-speed communication using a millimeter wave, and the specification of Japanese Patent No. 5725222, the specification of Japanese Patent No. 2516140, and Japanese Patent Application Laid-Open Publication No. 2015-19137 disclose forms of signal transmission using a millimeter wave.

SUMMARY OF THE INVENTION

An image pickup apparatus according to an aspect of the present invention includes: a first unit including an image pickup device configured to pick up an image of an object and generate a video signal; a second unit including a video processing circuit configured to perform predetermined processing on the video signal; a waveguide path that is provided between the first unit and the second unit and through which a millimeter wave or a submillimeter wave is transmitted; a millimeter-wave carrier wave generation circuit disposed in the second unit and configured to generate a millimeter-wave carrier wave based on a predetermined reference signal; a processing-transmission circuit disposed in the first unit and configured to receive the millimeter-wave carrier wave generated by the millimeter-wave carrier wave generation circuit in the second unit through the waveguide path, generate a millimeter-wave modulated wave by superimposing the video signal generated by the image pickup device on the millimeter-wave carrier wave, and transmit the millimeter-wave modulated wave toward the waveguide path; and a demodulator disposed in the second unit and configured to receive the millimeter-wave modulated wave generated in the first unit through the waveguide path and regenerate the video signal generated by the image pickup device.

An endoscope apparatus according to an aspect of the present invention includes the image pickup apparatus.

A mobile body according to an aspect of the present invention includes the image pickup apparatus.

An image pickup unit according to an aspect of the present invention is an image pickup unit connected to a waveguide path through which a millimeter wave is transmitted, the image pickup unit including: an image pickup device configured to pick up an image and generate a video signal; and a processing-transmission circuit configured to configured to generate a millimeter-wave modulated wave by superimposing the video signal generated by the image pickup device on a millimeter-wave carrier-wave signal received through the waveguide path and transmit the generated millimeter-wave modulated wave to the waveguide path.

A video processing unit according to an aspect of the present invention is a video processing unit connected to a waveguide path through which a millimeter wave is transmitted and including: a millimeter-wave carrier wave generation circuit configured to generate a millimeter-wave carrier wave based on a predetermined reference signal and send the millimeter-wave carrier wave to the waveguide path; and a demodulator configured to receive, through the waveguide path, a millimeter-wave modulated wave generated by superimposing a video signal on the millimeter-wave carrier wave and regenerate the video signal by demodulating the millimeter-wave modulated wave.

DETAILED DESCRIPTION OF THE PREFERRED EMBODIMENTS

Embodiments of the present invention will be described below with reference to the accompanying drawings.

Note that the present invention is not limited by the present embodiments. In description of the drawings, identical parts are denoted by the same reference sign. Note that each drawing is schematic, and thickness and width relations among members, ratios of the members, and the like are different from thickness and width relations among the members, ratios of the members, and the like in reality. The drawings include a part having a dimension or ratio that is different among the drawings.

First Embodiment

Figure 1:
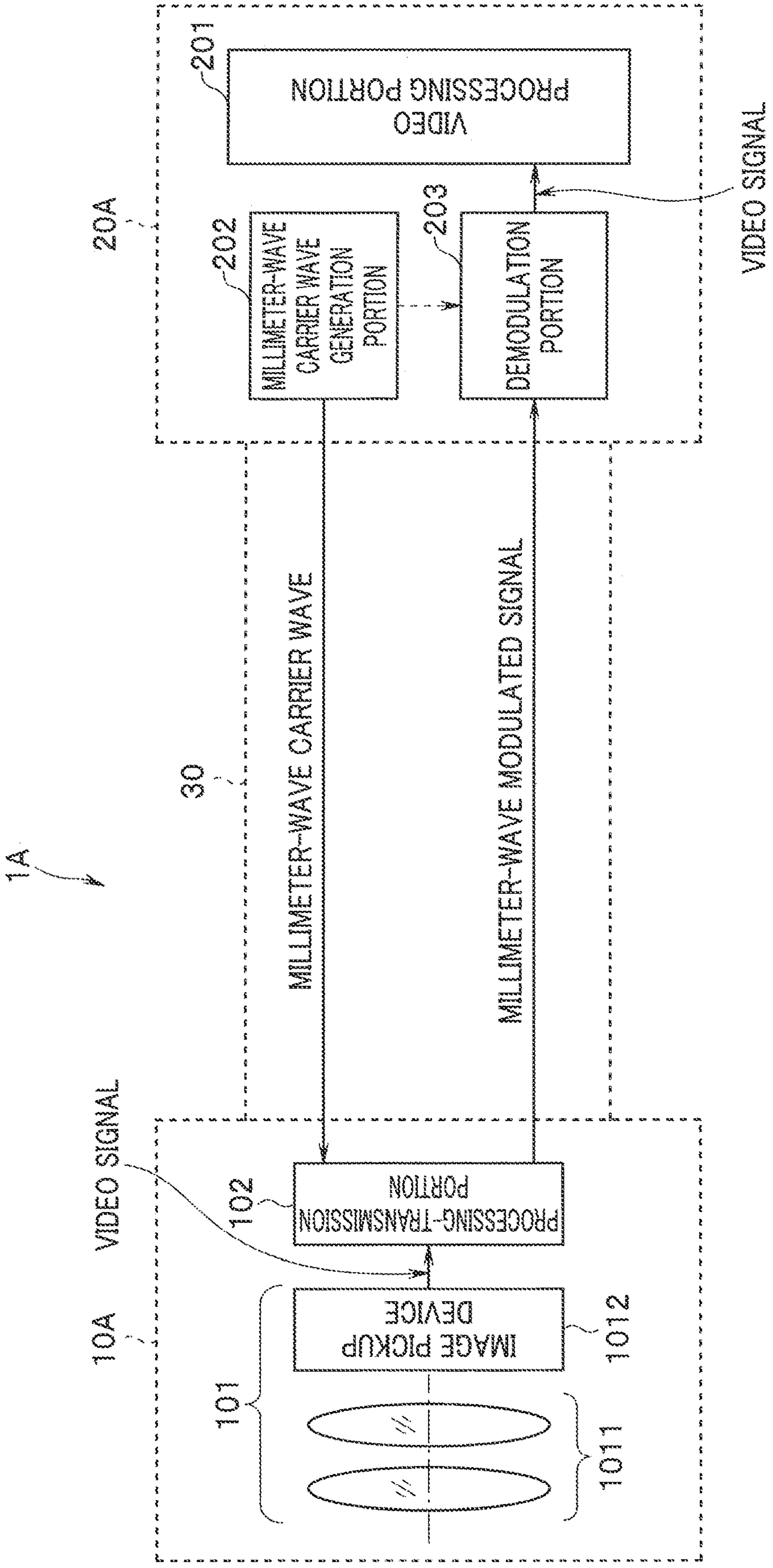
FIG. 1 is a block diagram illustrating a configuration of an image pickup apparatus of a first embodiment of the present invention.
Figure 2:
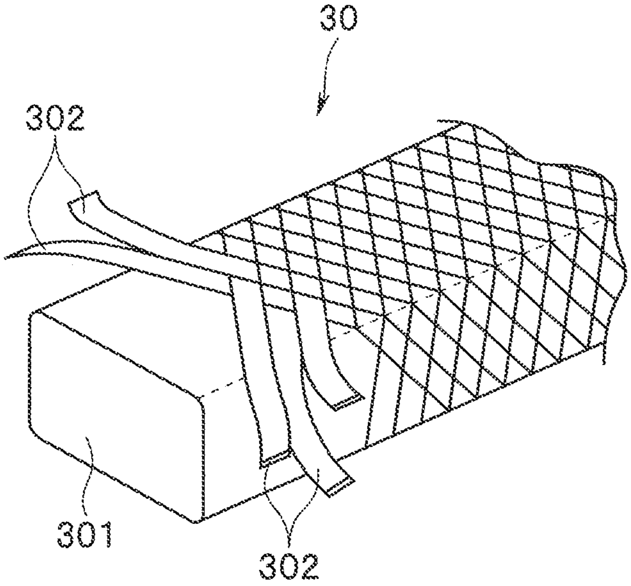
FIG. 2 is a main-part enlarged cross-sectional view illustrating a configuration of a waveguide pipe in the image pickup apparatus of the first embodiment.
Figure 3:
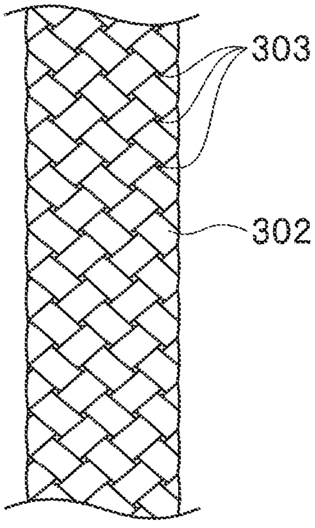
FIG. 3 is an exterior diagram illustrating an exterior of an outer conductor formed by twining flat foiled yarns in a braided cord shape in the waveguide pipe employed in the image pickup apparatus of the first embodiment.
Figure 4:
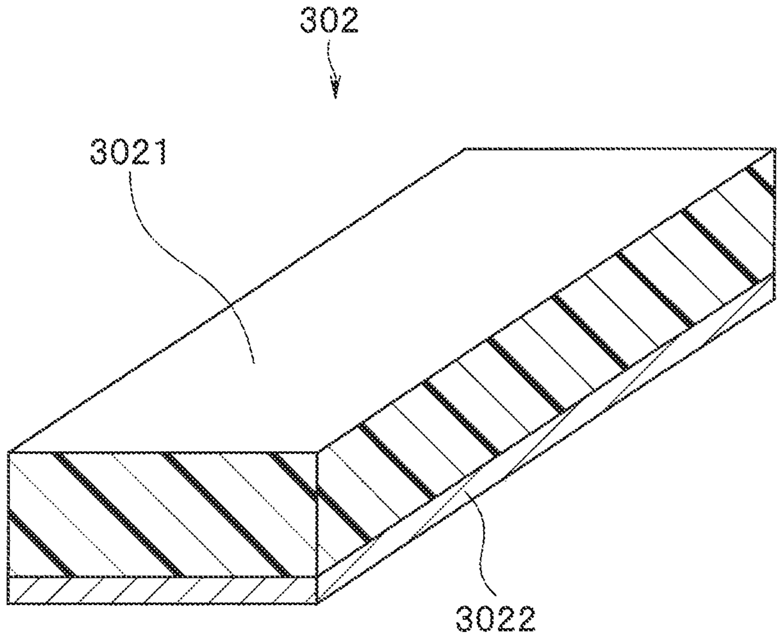
FIG. 4 is a main-part enlarged cross-sectional view illustrating a configuration of a flat foiled yarn included in the outer conductor in the waveguide pipe employed in the image pickup apparatus of the first embodiment.

FIG. 1 is a block diagram illustrating a configuration of an image pickup apparatus of a first embodiment of the present invention. FIG. 2 is a main-part enlarged cross-sectional view illustrating a configuration of a waveguide pipe in the image pickup apparatus of the first embodiment, FIG. 3 is an exterior diagram illustrating an exterior of an outer conductor formed by twining flat foiled yarns in a braided cord shape in the waveguide pipe employed in the image pickup apparatus of the first embodiment, and FIG. 4 is a main-part enlarged cross-sectional view illustrating a configuration of a flat foiled yarn in the waveguide pipe employed in the image pickup apparatus of the first embodiment.

As illustrated in FIG. 1, the image pickup apparatus 1A of the first embodiment includes a first unit (image pickup unit) 10A including an image pickup portion 101 configured to pick up an image of an object and generate a video signal, a second unit (video processing unit) 20A including a video processing portion (video processing circuit) 201 configured to perform predetermined processing on the video signal, and a waveguide path 30 that is provided between the first unit 10A and the second unit 20A and through which a millimeter wave or a submillimeter wave is transmitted.

<First Unit 10A>

The first unit 10A includes the above-described image pickup portion 101 and a processing-transmission portion 102. The image pickup portion 101 includes an image pickup optical system 1011 on which a subject image is incident, and an image pickup device 1012. The image pickup device 1012 is disposed on a back side of the image pickup optical system 1011, picks up the subject image, and outputs a predetermined video signal through photoelectric conversion.

The processing-transmission portion (processing-transmission circuit) 102 receives a millimeter-wave carrier wave generated by a millimeter-wave carrier wave generation portion of the second unit 20A through the waveguide path 30, generates a millimeter-wave modulated wave (millimeter-wave modulated signal) by superimposing the video signal generated by the image pickup portion 101 on the millimeter-wave carrier wave, and transmits the millimeter-wave modulated signal toward the waveguide path 30. A specific configuration of the processing-transmission portion 102 will be described later in detail.

In this manner, the first unit 10A is an image pickup unit connected to the waveguide path 30 through which a millimeter wave is transmitted, and includes the image pickup portion 101 configured to pick up an image and generate a video signal, and the processing-transmission portion 102 configured to generate a millimeter-wave modulated wave by superimposing the video signal generated by the image pickup portion 101 on a millimeter-wave carrier-wave signal received through the waveguide path 30 and transmit the generated millimeter-wave modulated wave to the waveguide path 30.

<Second Unit 20A>

The second unit 20A includes a millimeter-wave carrier wave generation portion 202 configured to generate the millimeter-wave carrier wave, a demodulation portion 203 configured to acquire a video signal based on the millimeter-wave modulated signal on which the video signal is superimposed and that is outputted from the first unit 10A, and the video processing portion 201 configured to perform predetermined processing on the acquired video signal.

The millimeter-wave carrier wave generation portion (millimeter-wave carrier wave generation circuit) 202 in the present embodiment includes a non-illustrated oscillation element or oscillation circuit. The millimeter-wave carrier wave generation portion 202 generates the millimeter-wave carrier wave based on a predetermined reference signal generated by the oscillation element or the oscillation circuit, and outputs the generated millimeter-wave carrier wave. Specifically, the millimeter-wave carrier wave is generated by, for example, multiplying the reference signal.

Note that the millimeter-wave carrier wave generation portion 202 may generate the millimeter-wave carrier wave through mixing (up-conversion) of another reference signal generated by another oscillation element or oscillation circuit.

The demodulation portion (demodulator) 203 receives the millimeter-wave modulated signal generated by the processing-transmission portion 102 in the first unit 10A through the waveguide path 30, and regenerates (restores) the video signal generated by the image pickup portion 101, by using a signal generated by the millimeter-wave carrier wave generation portion 202.

Note that components included in the second unit 20A are not necessarily unified as a unit.

In this manner, the second unit 20A is a video processing unit connected to the waveguide path 30 through which a millimeter wave is transmitted, and includes the millimeter-wave carrier wave generation portion 202 configured to generate a millimeter-wave carrier wave based on a predetermined reference signal and send the generated millimeter-wave carrier wave to the waveguide path 30, and the demodulation portion 203 configured to receive a millimeter-wave modulated wave generated by superimposing a video signal on the millimeter-wave carrier wave through the waveguide path 30 and regenerate the video signal by demodulating the received millimeter-wave modulated wave.

<Waveguide Path 30>

As illustrated in FIGS. 2 and 3, the waveguide path 30 in the present embodiment is configured as, for example, a flexible waveguide pipe, and specifically configured as a waveguide pipe including a flexible internal dielectric 301 extending with a dielectric constant that is uniform in a longitudinal direction, and an outer conductor 302 that is a flexible metal layer covering an outer periphery of the dielectric continuously extending in the longitudinal direction.

As illustrated in FIG. 2, the internal dielectric 301 in the present embodiment is a linear dielectric having a uniform dielectric constant in a longitudinal direction and having a section that is orthogonal to the longitudinal direction and has a constant shape in the longitudinal direction, and the section orthogonal to the longitudinal direction has a major radius and a minor radius (for example, an oval shape).

The outer conductor 302 is formed by winding a plurality of flat foiled yarns around the outer periphery of the internal dielectric 301 at, for example, 45° and twining the flat foiled yarns in a braided cord shape as illustrated in FIGS. 2 and 3, the flat foiled yarns being made of a composite material of a metal foil 3022 and a resin film 3021 as illustrated in FIG. 4.

Note that, in the present embodiment, a "uniform dielectric constant" is uniform in a magnitude of a wavelength order of electric waves (millimeter waves or submillimeter waves) propagating inside the waveguide pipe. Specifically, dielectric constant distribution due to a structure having dimensions different from the wavelength order by one or two digits or more does not affect electric waves propagating inside the waveguide pipe and thus is included in the uniform dielectric constant in the present embodiment.

Configurations of the waveguide path (waveguide pipe) 30 employed in the image pickup apparatus 1A of the present embodiment, its peripheral circuits, and the like will be described below in detail.

In the present embodiment, the waveguide path 30 is configured as, for example, a flexible waveguide pipe as described above and is a waveguide path that is a signal transmission path connecting the first unit 10A and the second unit 20A and through at least part of which a millimeter wave or a submillimeter wave propagates.

Specifically, the waveguide path 30 in the present embodiment newly provides, in place of a lead-wire signal transmission scheme or an optical-fiber signal transmission scheme that has been conventionally used, a signal transmission scheme using a waveguide path (flexible waveguide pipe) through which a millimeter wave or a submillimeter wave (electric wave having a frequency of 30 to 600 GHz approximately) passes as a signal transmission scheme for connecting an image pickup portion (in the present embodiment, the first unit 10A) and a video processing portion (in the present embodiment, the second unit 20A) in an image pickup apparatus or the like.

Note that a millimeter wave and a submillimeter wave in the present embodiment are electric waves having a wavelength of a millimeter to submillimeter order (0.5 to 10 mm approximately).

<Internal Dielectric and Outer Conductor of Flexible Waveguide Pipe>

The internal dielectric and the outer conductor of the flexible waveguide pipe 30 in the present embodiment will be described below in detail.

The flexible waveguide pipe in the present embodiment includes a dielectric material that appropriately satisfies two conditions of small dielectric loss tangent and appropriate flexibility, and is used in a millimeter-wave region (including a submillimeter wave) and configured as a waveguide path through which a millimeter wave or a submillimeter wave (hereinafter representatively referred to as a millimeter wave in some cases) passes.

<Configuration of Internal Dielectric>

As described above, the internal dielectric 301 in the present embodiment is a linear dielectric having a uniform dielectric constant in the longitudinal direction and having a section that is orthogonal to the longitudinal direction and has a constant shape in the longitudinal direction as illustrated in FIG. 2, and it is assumed that the internal dielectric

301 is made of, for example, a flexible dielectric material such as foamed polytetrafluoroethylene (PTFE) or foamed polyethylene.

Alternatively, the internal dielectric 301 may be made of a dielectric mixed material as a mixture of a resin material (for example, PTFE, or non-polar resin such as polyethylene), which is a parent material, and a crystalline material (for example, powder of a crystalline material having a small dielectric loss, such as α alumina).

As a modification, the internal dielectric may have a configuration as described below although not illustrated. Specifically, for example, the internal dielectric 301 may include a first dielectric positioned on a relatively inner side at a section orthogonal to the longitudinal direction, and a second dielectric positioned on an outer side of the first dielectric at the section orthogonal to the longitudinal direction (and disposed to cover an entire perimeter of an outer peripheral part of the first dielectric) and having a dielectric constant lower than a dielectric constant of the first dielectric.

In the modification, the internal dielectric is formed by filling a continuous pipe-shaped space at a center of the second dielectric in the longitudinal direction with the first dielectric formed of crystal powder. Note that the pipe-shaped space has a section of a shape (for example, an oval shape) having a major radius and a minor radius.

The crystal powder in the first dielectric is highly pure α-$Al_2O_3$ crystal powder (in the present modification, highly pure alumina AA-18: purity=99.99% or higher, manufactured by Sumitomo Chemical Co., Ltd.). The highly pure α-$Al_2O_3$ crystal powder has, for example, a substantially spherical shape of an average diameter of 18 μm approximately. Note that the first dielectric is made of the alumina crystal powder and maintains a shape when filling the pipe-shaped space in the second dielectric.

The second dielectric is made of stretched foamed PTFE (PTFE inside and on a surface of which continuous pores are formed through stretching in the longitudinal direction) and has a continuous pipe-shaped space at the center in the longitudinal direction.

The size (diameter) of each highly pure α-$Al_2O_3$ crystal in the first dielectric is larger than the size of each continuous pore in the second dielectric, and thus the α-$Al_2O_3$ crystal cannot pass through the continuous pore.

<Configuration of Outer Conductor>

The outer conductor 302 in the present embodiment is disposed at a position where the outer conductor 302 covers the outer periphery of the internal dielectric 301 as illustrated in, for example, FIG. 2, and is formed as a flexible tubular metal layer part. Specifically, the outer conductor 302 is formed of a plurality of strip-shaped flat foiled yarns as described above.

As illustrated in FIG. 4, each strip-shaped flat foiled yarn has a rectangular section orthogonal to the longitudinal direction and includes an underlayer 3021 containing a non-metal material such as resin, and the metal foil 3022 containing a metal material. More specifically, the flat foiled yarn is formed in a strip shape having a width of 0.2 mm with the underlayer being a resin film (for example, PET) having a thickness of 25 μm and with the metal foil being a copper foil having a thickness of 9 μm.

The outer conductor 302 in the present embodiment is formed by twining a plurality (for example, 32) of flat foiled yarns in a cylindrical braided cord shape. Specifically, the flat foiled yarns are wound around an outer peripheral surface of the internal dielectric with the metal foil being disposed and extended on a side contacting the dielectric, and are knitted to form a braided cord shape form.

Note that the outer conductor 302 includes a predetermined metal layer part (metal foil) as described above, and a conductive rate of the metal foil is set to be $59\times10^6$ S/m, which is equivalent to a conductive rate of pure copper. Note that although a conductive rate is uniquely determined in this example, the conductive rate of the metal layer part is not limited to this configuration in the present invention, and a metal layer having a high conductive rate is preferably used in the embodiment.

Note that, in each flat foiled yarn as the outer conductor 302 in the present embodiment, the metal foil is disposed on a side contacting the second dielectric and the resin film is disposed on an outer side as described above, but the flat foiled yarn is not limited to this configuration but may be configured in another form including a metal layer (for example, a three-layer structure in which the metal layer is sandwiched between resins).

Note that although the outer conductor 302 has a predetermined thickness in, for example, FIG. 2, each drawing is schematic as described above, and thickness and width relations among members, a ratio of the members, and the like are different from actual thickness and width relations among the members, a ratio of the members, and the like, and specifically, the outer conductor 302 is formed of a sufficiently thin metal foil actually.

As described above, the internal dielectric 301 in the present embodiment is configured so that a sectional shape of the internal dielectric 301 can be easily maintained, and accordingly, achieves an effect that a transmission mode of an electric wave transmitted inside the dielectric can be stabilized.

Moreover, since the internal dielectric 301 is extended in a sectional shape that is constant in the longitudinal direction as described above, the flexible waveguide pipe 30 achieves an effect that, when the waveguide pipe itself is bent by external force applied from outside, increase of a transmission loss attributable to the bending is reduced, and as a result, a transmission loss amount is stabilized.

In the above-described modification of the internal dielectric, the second dielectric is disposed to cover the entire perimeter of the outer peripheral part of the first dielectric and disposed in a region sandwiched between the first dielectric and the outer conductor 302 as the metal layer.

In the modification, the second dielectric has a dielectric constant lower than a dielectric constant of the first dielectric. In other words, since the dielectric constant of the first dielectric is higher than the dielectric constant of the second dielectric and the second dielectric is disposed to cover the entire perimeter of the outer peripheral part of the first dielectric, energy of an electromagnetic wave transmitted inside the flexible waveguide pipe 30 can be contained in the first dielectric.

As a result, generation of a transmission loss attributable to an outer conductor 302 as the metal layer can be prevented in the flexible waveguide pipe 30 of the present embodiment.

<Specific Example of Processing-Transmission Portion 102>

Subsequently, specific examples of a configuration (processing-transmission portions 102A and 102B) of the processing-transmission portion 102 in the first unit 10A will be described below with reference to FIGS. 5 and 6, respectively.

<First Example of Configuration of Processing-Transmission Portion 102; Processing-Transmission Portion 102A>

Figure 5:
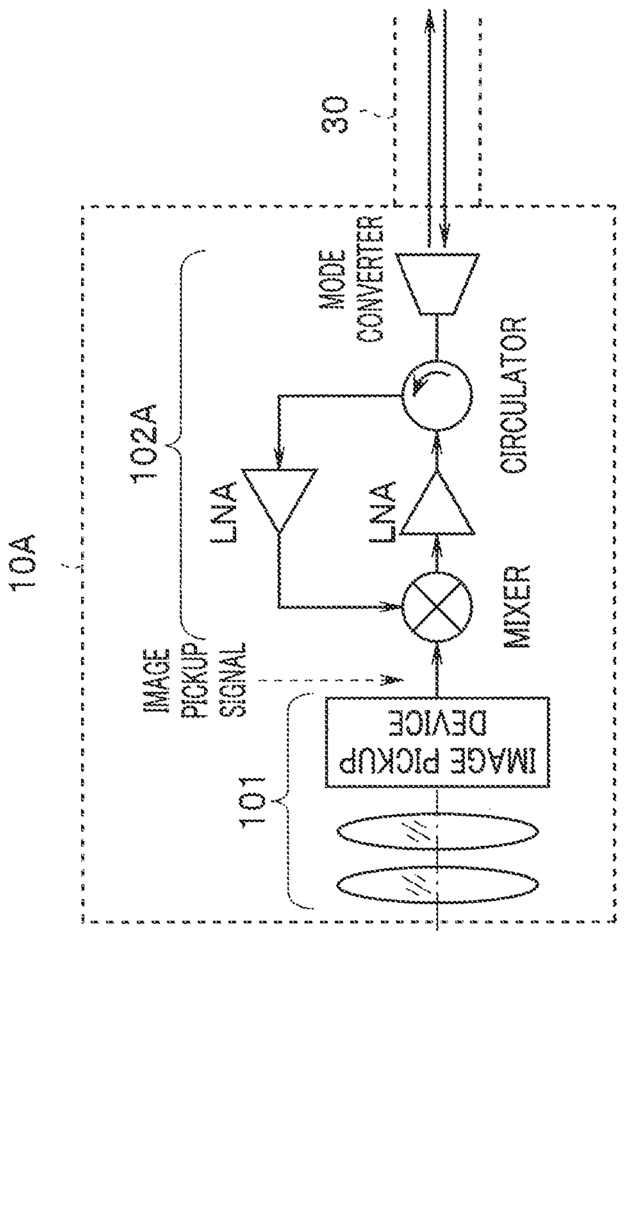
FIG. 5 is a block diagram illustrating a specific configuration of a processing-transmission portion in a first unit in the image pickup apparatus of the first embodiment.

FIG. 5 is a block diagram illustrating a specific configuration of the processing-transmission portion in the first unit in the image pickup apparatus of the first embodiment.

In the first embodiment, the processing-transmission portion 102 in the first unit 10A includes a modulator of what is called on-off keying (OOK) or amplitude shift keying (ASK) as in the processing-transmission portion 102A illustrated in FIG. 5.

The processing-transmission portion 102A receives a millimeter-wave carrier wave generated by the millimeter-wave carrier wave generation portion 202 in the second unit 20A through the waveguide path 30, and in this case, the millimeter-wave carrier wave is acquired into a circuit at a later stage through a mode convertor and a circulator.

In addition, the processing-transmission portion 102A can obtain a millimeter-wave modulated signal as an OOK modulated signal or an ASK modulated signal by superimposing an image pickup signal on the received millimeter-wave carrier wave at a mixer (multiplier).

Thereafter, the millimeter-wave modulated signal on which the image pickup signal is superimposed is transmitted into the waveguide path 30 through the mode convertor.

An attention should be paid to a configuration in which the processing-transmission portion 102A as a side for transmitting a video signal includes no circuit configured to oscillate at millimeter-wave frequencies. This configuration is a characteristic of the present application invention and clearly different from a transmission-reception circuit used in a conventional image pickup apparatus as disclosed in, for example, Japanese Patent Application Laid-Open Publication No. 2011-39340 and the specification of Japanese Patent No. 5725222, and largely contributes to circuit size reduction.

Moreover, the mixer (multiplier) can be configured as an extremely simple circuit, which leads to circuit size reduction. Thus, communication with OOK modulation or ASK modulation is highly advantageous when size and weight reduction is important, in particular.

Note that, to achieve signal amplification, a low noise amplifier (LNA) is inserted in the processing-transmission portion 102A, but may be omitted when signal intensity does not need to be improved, in particular. Similarly, the circulator and the mode convertor are not limited to the above-described disposition, but the same function can be obtained with a configuration in which the circulator is omitted and a plurality of waveguide paths 30 are provided, a configuration in which the circulator and the mode convertor are replaced with another means, or the like.

Note that circuit requirements needed in association exist in actual circuits, but the present example describes a basic concept, and thus the circuit requirements are omitted in the description. These omitted elements need to be added and used as necessary in reality.

<Second Example (Modification) of Configuration of Processing-Transmission Portion 102; Processing-Transmission Portion 102B>

Figure 6:
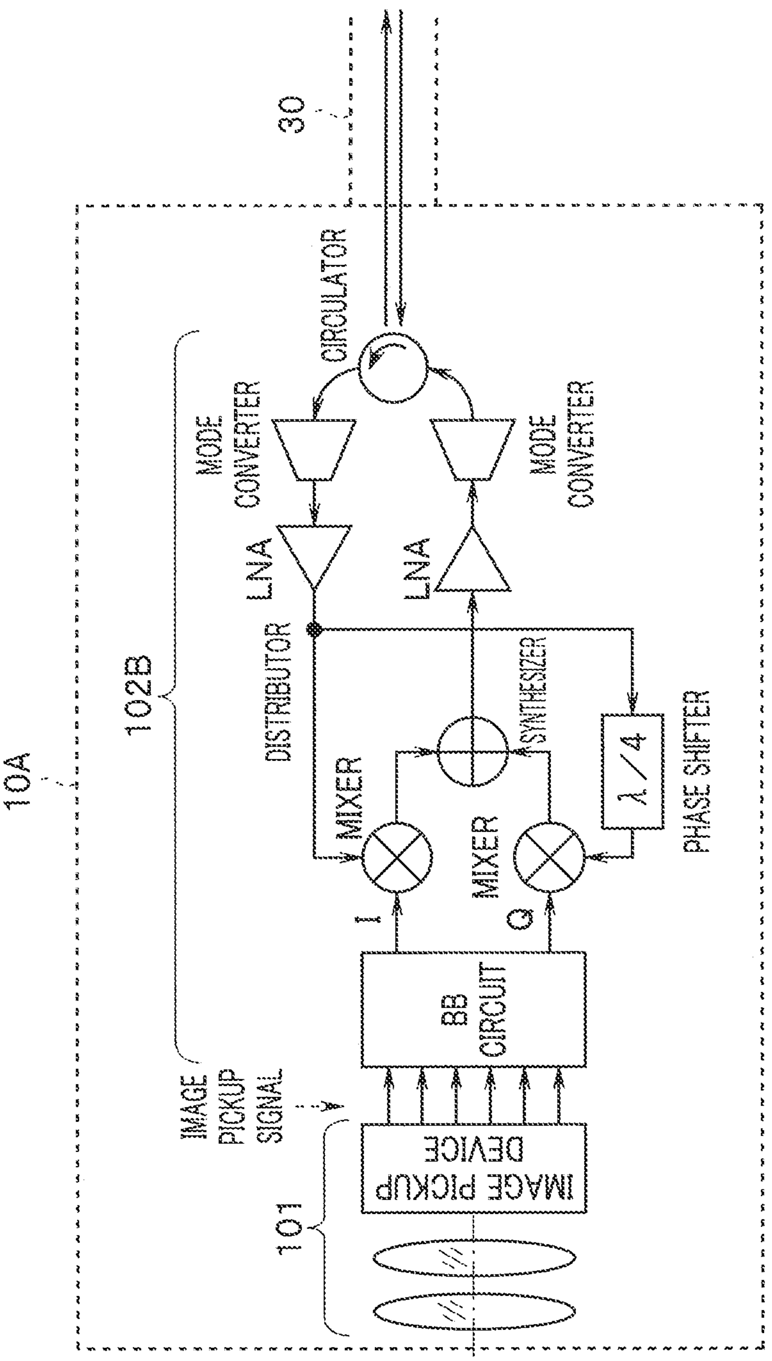
FIG. 6 is a block diagram illustrating another exemplary configuration of the processing-transmission portion in the first unit in the image pickup apparatus of the first embodiment.

FIG. 6 is a block diagram illustrating another example of the configuration of the processing-transmission portion in the first unit in the image pickup apparatus of the first embodiment.

The processing-transmission portion 102 in the first unit 10A in the first embodiment may have a configuration of the processing-transmission portion 102B illustrated in FIG. 6 as a modification.

Specifically, the processing-transmission portion 102B as a modification of the processing-transmission portion 102A includes a modulator of what is called quadrature amplitude modulation (QAM).

Similarly to the above-described configuration of the processing-transmission portion 102A (refer to FIG. 5), the processing-transmission portion 102B receives a millimeter-wave carrier wave generated by the millimeter-wave carrier wave generation portion 202 in the second unit 20A through the waveguide path 30.

The processing-transmission portion 102B of the modification acquires the received millimeter-wave carrier wave into a circuit at a later stage by a mode convertor through a circulator first. Thereafter, the processing-transmission portion 102B separates the acquired millimeter-wave carrier wave into two lines through a distributor.

Thereafter, the processing-transmission portion 102B directly receives, at one of mixers (multipliers), a part of the millimeter-wave carrier wave separated through the distributor, and shifts a phase of the other part of the millimeter-wave carrier wave by $\lambda/4$ through a phase shifter, and then receives the other part at the other mixer (multiplier) and superimposes a video signal on the other part.

The processing-transmission portion 102B converts, at a base band circuit (BB circuit), a received video signal into I-Q signals necessary for quadrature amplitude modulation. The 1-Q signals are received by the respective mixers (multipliers), and modulated wave signals on which the I-Q signals are superimposed, respectively, are generated and then subjected to addition processing at a synthesizer. Accordingly, a millimeter-wave modulated signal as a quadrature amplitude modulation (QAM) signal is generated.

Thereafter, the millimeter-wave modulated signal on which an image pickup signal is superimposed is transmitted into the waveguide path 30 through a mode convertor and a circulator.

A circuit configuration of the processing-transmission portion 102B (refer to FIG. 6) of the modification is complicated as compared to a circuit configuration of the processing-transmission portion 102A (refer to FIG. 5), but communication with quadrature amplitude modulation is advantageous for signal speed improvement and is a method that is extremely advantageous for achieving communication at 10 Gbps or higher, in particular.

Thus, communication with quadrature amplitude modulation (QAM) is highly advantageous when communication speed increase is important, in particular.

Moreover, the processing-transmission portion 102A including the modulator of OOK modulation or ASK modulation as illustrated in FIG. 5 and the processing-transmission portion 102B including the modulator of quadrature amplitude modulation (QAM) as illustrated in FIG. 6 have particularly useful circuit configurations having characteristics different from each other.

However, which circuit configuration is more preferable should be selected based on requirements for an image pickup instrument, and is a designing requirement.

Note that the processing-transmission portion 102B includes the LNAs, the circulator, and the mode convertors as well as elements omitted in description and illustrations, and these components have roles same as in a case of the processing-transmission portion 102A, and thus their necessities, configurations, and numbers are designing requirements.

For example, in each of circuit examples illustrated in FIGS. 5 and 6, the millimeter-wave carrier wave generated in the second unit 20A and the millimeter-wave modulated signal generated by the first unit 10A are transmitted and received through one waveguide path 30 by using the circulator, but two mode convertors and two waveguide paths 30 may be provided, in other words, mode convertors and waveguide paths dedicated for the millimeter-wave carrier wave and the millimeter-wave modulated signal are provided without using the circulator.

Note that, similarly to the processing-transmission portion 102A, the processing-transmission portion 102B as a side for transmitting a video signal include no circuit configured to oscillate at millimeter-wave frequencies, which largely contributes to circuit size reduction.

Configurations of the present embodiment are described above. Circuit requirements needed in association exist in actual circuits, but the present example describes a basic concept, and thus the circuit requirements are omitted in the description. The omitted elements need to be added and used as necessary actually.

<Effects of First Embodiment>

Effects of the first embodiment will be described below along a signal flow.

<Carrier-Wave Generation=Processing in Second Unit>

Transmission of a video signal in the image pickup apparatus 1A is performed by using a millimeter-wave electric wave. Specifically, the video signal is superimposed on a millimeter-wave carrier wave and transferred.

The millimeter-wave carrier wave is generated by the millimeter-wave carrier wave generation portion 202 in the second unit 20A as described above. The millimeter-wave carrier wave is generated by multiplying a reference signal generated by a non-illustrated oscillation element or oscillation circuit. Alternatively, the millimeter-wave carrier wave is generated through mixing (up-conversion) of another reference signal generated by another oscillation element or oscillation circuit.

Thereafter, the millimeter-wave carrier wave generated in the second unit 20A (millimeter-wave carrier wave generation portion 202) are transmitted into the waveguide path 30 through a non-illustrated mode convertor.

Note that the millimeter-wave carrier wave generated by the millimeter-wave carrier wave generation portion 202 or the reference signal generated through a process of the millimeter-wave carrier wave generation is also used in video signal demodulation as described later.

<Image Pickup to Modulation Processing and Transmission=Processing in First Unit>

In the image pickup apparatus 1A of the first embodiment, when a subject image is incident on the image pickup optical system 1011, the image pickup device 1012 picks up the subject image and outputs a predetermined video signal through photoelectric conversion.

In the processing-transmission portion 102 (processing-transmission portion 102A (refer to FIG. 5) or processing-transmission portion 102B (refer to FIG. 6)), the video signal outputted from the image pickup device 1012 is provided with processing and conversion into a signal form suitable for millimeter-wave transmission and also provided with mixing processing with a millimeter-wave carrier wave. Accordingly, a millimeter-wave modulated signal is generated and transmitted toward the waveguide path 30.

Note that the millimeter-wave carrier wave is generated in the second unit 20A described above and received through the waveguide path 30, but not generated in the first unit 10A.

Specifically, for example, the processing-transmission portion 102A illustrated in FIG. 5 receives a millimeter-wave carrier wave generated by the millimeter-wave carrier wave generation portion 202 in the second unit 20A through the waveguide path 30. Then, the received millimeter-wave carrier wave is acquired into a circuit at a later stage through the mode convertor and the circulator.

The processing-transmission portion 102A superimposes, at the mixer (multiplier), an image pickup signal outputted from the image pickup portion 101 on the millimeter-wave carrier wave acquired through the mode convertor and the circulator. Thereafter, the processing-transmission portion 102A transmits, into the waveguide path 30, a millimeter-wave modulated signal (OOK modulated signal or ASK modulated signal) on which the image pickup signal is superimposed.

Similarly to the above description, the processing-transmission portion 102B illustrated in FIG. 6 receives a millimeter-wave carrier wave generated by the millimeter-wave carrier wave generation portion 202 in the second unit 20A through the waveguide path 30. Then, the received millimeter-wave carrier wave is acquired into a circuit at a later stage through the circulator and a mode convertor.

The processing-transmission portion 102B first separates the millimeter-wave carrier wave acquired through the circulator and the mode convertor into two lines at the distributor. Thereafter, a part of the separated millimeter-wave carrier wave is directly guided to one of the mixers (multipliers), and the other part of the millimeter-wave carrier wave is guided to the other mixer (multiplier) in a state in which a phase of the other part is shifted by $\lambda/4$ through the phase shifter. Each mixer in the processing-transmission portion 102B superimposes this separated signal guided to the mixer on an I-Q signal (signal including a video signal used in quadrature amplitude modulation) output from the BB circuit (base band circuit).

After generated as described above, modulated waves on which the I-Q signals are superimposed are subjected to addition processing at the synthesizer. Accordingly, a millimeter-wave modulated signal is generated as a quadrature amplitude modulation (QAM) signal.

Thereafter, the processing-transmission portion 102B transmits, into the waveguide path 30, the millimeter-wave modulated signal (quadrature amplitude modulation signal) on which an image pickup signal is superimposed.

<Demodulation=Processing in Second Unit>

The millimeter-wave modulated signal received by the second unit 20A through the waveguide path 30 is introduced into the demodulation portion 203 through a non-illustrated mode convertor. Thereafter, the millimeter-wave modulated signal is subjected to detection and demodulation processing at the demodulation portion 203 to restore a video signal generated by the image pickup portion 101 in the first unit 10A.

Detection and demodulation processing, in other words, video signal restoration needs a signal having a frequency equal to a frequency of the millimeter-wave carrier wave, but in the detection and demodulation processing in the present embodiment, a signal having a frequency equal to the frequency of the millimeter-wave carrier wave or a signal used to generate the millimeter-wave carrier wave is introduced from the millimeter-wave carrier wave generation portion 202 disposed in the same second unit 20A, and is used for the detection and demodulation processing.

Note that, in this method, the millimeter-wave carrier wave and the signal (signal having a frequency equal to the frequency of the millimeter-wave carrier wave or signal used to generate the millimeter-wave carrier wave) used for detection and demodulation are originated from the same signal (signal generated by the millimeter-wave carrier wave generation portion 202), and thus difference is unlikely to occur between their frequencies. Thus, sizes of units related to transmission and reception can be reduced because high stability is not necessarily required for the carrier-wave frequency.

<Video Processing=Processing in Second Unit>

A video signal restored by the demodulation portion 203 is provided with predetermined processing at the video processing portion 201. The predetermined processing includes, for example, compression processing for facilitating handling of a significantly large amount of video information, storage or transmission processing, or processing of converting information into a form suitable for image display.

<Problem With Conventional Millimeter-Wave Communication System and Circuit Scale Reduction in the Present Invention>

As indicated with reference to a problem with Japanese Patent Application Laid-Open Publication No. 2011-39340 described above, high stability is required for the carrier-wave frequency in millimeter-wave communication, and thus a complicated oscillation circuit having high frequency stability is needed, which is likely to result in size increase of units related to transmission and reception. This problem will be described below in more detail together with supplementary description of how the problem is solved by the present invention.

In millimeter-wave communication by a scheme used in typical wireless communication, high stability in an order of ppm is required for a carrier frequency. This is because a signal cannot be correctly demodulated when there is a difference between a frequency used for signal carriage and a frequency used for demodulation, and this frequency difference for millimeter waves needs to be at the order of ppm or lower.

A circuit scale increases when the required carrier-frequency stability is achieved by using, for example, a crystal oscillator, a frequency multiplication circuit, and a PLL circuit. Furthermore, when the required carrier-frequency stability is achieved by using a resonance circuit including an inductor and a capacitor, it is practically difficult to form an oscillation circuit that satisfies the requirement in an integrated circuit, and accordingly, the oscillation circuit that satisfies the requirement needs to be placed outside the integrated circuit, which increases the circuit scale as well.

The circuit scale can be reduced by using an injection signal disclosed in Japanese Patent Application Laid-Open Publication No. 2011-39340 and the specification of Japanese Patent No. 5725222, but in this case, although the requirement for the oscillation circuit is moderated, the number of circuits configured to generate a demodulation reference signal by using the injection signal increases, and the entire circuit scale remains large.

Thus, a circuit configuration in a millimeter-wave communication system is typically complicated, and accordingly, a system configuration as a whole is complicated as well.

However, in the present invention, firstly, size and weight reduction of the first unit (image pickup unit) is achieved since a generation portion (oscillation portion) of a carrier wave used in signal transmission is provided in the second unit (video processing unit).

In addition, a requirement for frequency stability of a millimeter-wave carrier wave and a signal used for detection and demodulation is significantly moderated since the same circuit (millimeter-wave carrier wave generation portion 202) generates the millimeter-wave carrier wave and provides the signal used for detection and demodulation. Accordingly, with a configuration of the present embodiment, it is possible to significantly reduce a scale of circuits necessary for millimeter-wave signal generation in an image pickup apparatus, including the first unit and the second unit.

<Supplementary Description of Configuration of Waveguide Path 30>

When high-speed communication at 10 Gbps or higher is considered, in particular, a transmission line needs to have a configuration with which noise superimposition is unlikely to occur in order to achieve a "configuration including a carrier-wave generation circuit in the second unit" in the present invention.

The present invention is premised on that the waveguide path 30 has a configuration including the dielectric 301 extending with a uniform dielectric constant in the longitudinal direction and the outer conductor (metal layer) covering the outer periphery of the dielectric continuously extending in the longitudinal direction, and research by the present inventor has found that a waveguide path having the present configuration is extremely unlikely to suffer noise superimposition and most excellent as a wired electric-wave communication means in the present invention (no configuration other than the present configuration is possible in effect).

In addition, since high-speed communication at several tens Gbps or higher is difficult to achieve as a conventional wired communication using a metal wire, an optical communication line is typically rigid and less flexible, and an optical-communication transmission-reception unit is extremely expensive as described above, the present configuration is best in effect as the configuration of the waveguide path in the image pickup apparatus of the present invention.

<Effects of Present Embodiment>

In the image pickup apparatus of the first embodiment, significant size and weight reduction of the first unit (image pickup unit) can be achieved, in particular, since the second unit (video processing unit) includes a generation portion (oscillation portion) configured to generate a reference signal from which a millimeter-wave carrier wave used for signal transmission is originated.

Moreover, a requirement for frequency stability of the reference signal can be significantly moderated to significantly reduce a circuit scale of a reference signal generation portion and appropriately transmit a high-speed image pickup signal. Accordingly, an image pickup apparatus including an image pickup portion of a reduced size and a reduced weight, in particular, and capable of reliably transmitting a large-volume image pickup signal with a configuration of a small circuit scale can be obtained.

Effects obtained by a high-speed image pickup apparatus having a configuration of a small circuit scale, which is described in the present embodiment, cannot be achieved by any other communication means, and the image pickup apparatus has an extremely large value as an image pickup means in a popular price range.

Second Embodiment

Subsequently, a second embodiment of the present invention will be described below.

An image pickup apparatus of the second embodiment has a main configuration same as in the first embodiment, but the second unit includes a delay circuit, which is a difference from the first embodiment. Thus, only the difference from the first embodiment will be described below, and description of any common part is omitted.

Figure 7:
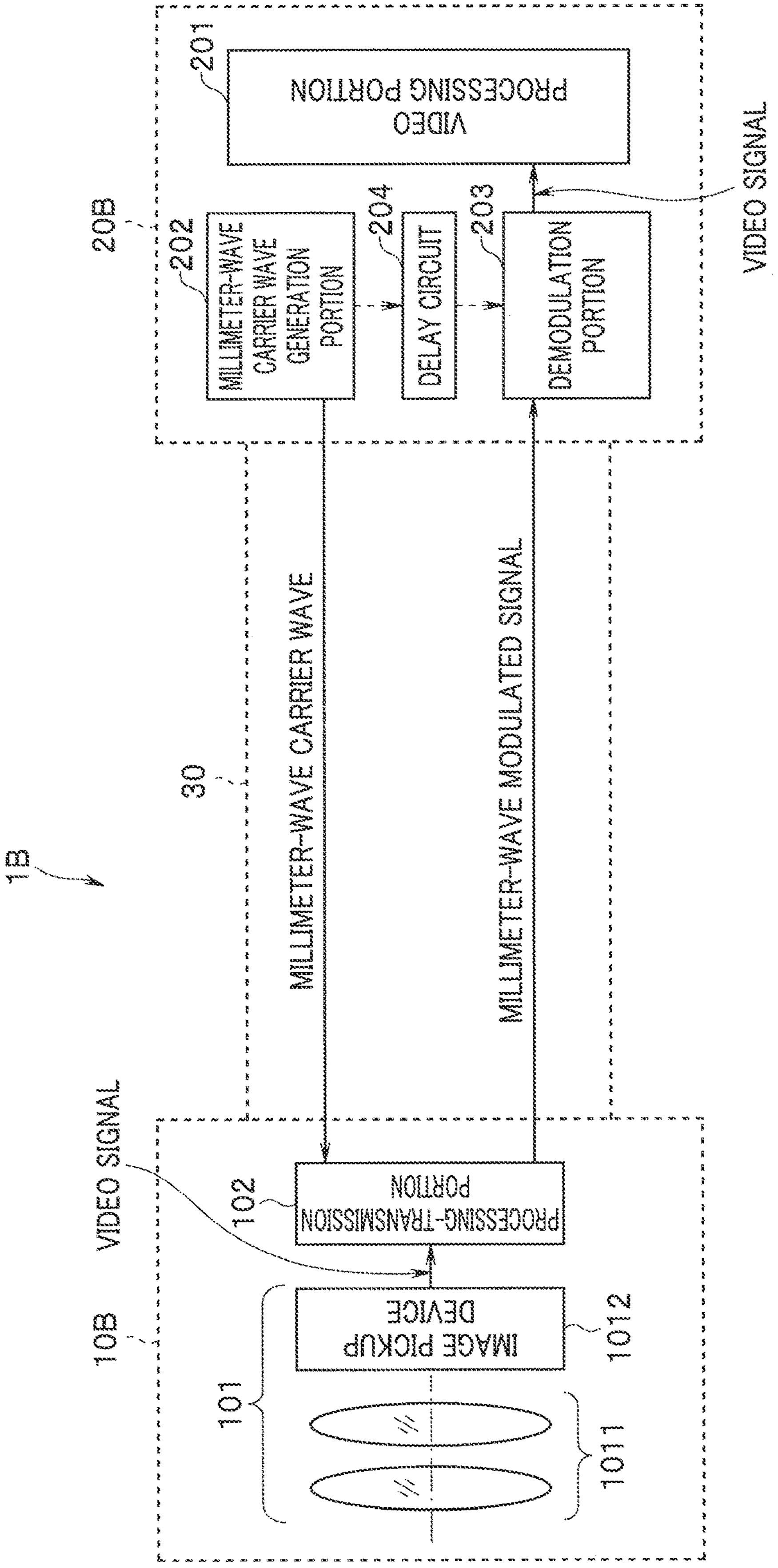
FIG. 7 is a block diagram illustrating a configuration of an image pickup apparatus of a second embodiment of the present invention.

FIG. 7 is a block diagram illustrating a configuration of the image pickup apparatus of the second embodiment of the present invention.

As illustrated in FIG. 7, an image pickup apparatus 1B of the second embodiment includes a first unit 10B having a configuration same as a configuration of the first unit 10A in the first embodiment, but a second unit 20B includes a delay circuit 204, which is a difference from the configuration of the first embodiment.

The delay circuit 204 has a function to provide a delay time period to a signal used for detection and demodulation (signal having a frequency equal to the frequency of a millimeter-wave carrier wave or signal used to generate the millimeter-wave carrier wave) before the demodulation portion 203 receives the signal used for detection and demodulation from the millimeter-wave carrier wave generation portion 202.

Effects of the delay circuit 204 will be described below in more detail.

As described above, the signal used for detection and demodulation by the demodulation portion 203 is a signal used to generate a millimeter-wave carrier wave by the millimeter-wave carrier wave generation portion 202 or is the millimeter-wave carrier wave, and thus can have a frequency basically equal to a frequency of the millimeter-wave carrier wave.

More precisely, the frequency of the millimeter-wave carrier wave generated by the millimeter-wave carrier wave generation portion 202 temporally varies due to influence of temperature and the like, and thus the millimeter-wave carrier wave used to generate a millimeter-wave modulated wave to be received by the demodulation portion 203 is a signal generated earlier by a time period of a round-trip through the waveguide path 30. Without any countermeasure, frequency difference corresponding to temporal frequency variation having occurred in the time period would be generated.

The delay circuit 204 in the second embodiment compensates the frequency difference corresponding to the temporal frequency variation by providing, to the signal used for detection and demodulation by the demodulation portion 203, a delay corresponding to the time period of a round-trip through the waveguide path 30.

Specifically, by using the delay circuit 204 in the second embodiment, the demodulation portion 203 can obtain the signal used for detection and demodulation and having a frequency precisely equal to a frequency of a carrier-wave component of a detection-demodulation target millimeter-wave modulated signal.

<Technological Meaning of Delay Circuit>

A function of the delay circuit 204 in the second embodiment is clearly different from a function of a phase adjustment portion in a technology disclosed in Japanese Patent Application Laid-Open Publication No. 2015-19137. The phase adjustment portion in Japanese Patent Application Laid-Open Publication No. 2015-19137 has a function to align a “phase” of a reference signal, but the delay circuit 204 in the second embodiment is provided to use, for detection and demodulation, signals oscillated at a same timing, in other words, has a function to align “times” of signals used for demodulation.

As described above, at a timing of reception by the second unit 20B, a millimeter-wave modulated wave on which a video signal is superimposed has a delay time period equal to the time period of a round-trip through the waveguide path 30 (precisely, including a time taken for processing in the first unit 10B), and the delay time period is constant because the waveguide path 30 is a wired line having a determined line length.

The delay circuit 204 in the second embodiment only needs to have a function to generate the constant delay time period, and the function can be simply achieved by a line having a length equivalent to a length of the waveguide path 30.

Note that processing, such as the phase adjustment, necessary for signal frequency conversion, detection, and demodulation needs to be added to a signal through the delay circuit 204 as necessary in the present invention, and the addition is a designing matter.

<Effects of Second Embodiment>

In addition to the effects of the first embodiment, the image pickup apparatus of the second embodiment can further increase stability of detection and demodulation. Specifically, the delay circuit 204 is provided to eliminate carrier frequency mismatching due to temporal variation of a frequency of a millimeter-wave carrier wave, and thus an image pickup apparatus having increased stability of detection and demodulation and thus increased stability of image pickup can be obtained.

Third Embodiment

Subsequently, a third embodiment of the present invention will be described below.

An image pickup apparatus of the third embodiment has a main configuration same as in the first embodiment, but the first unit includes an electric power generation portion, which is a difference from the first embodiment. Thus, only the difference from the first embodiment will be described below, and description of any common part is omitted.

Figure 8:
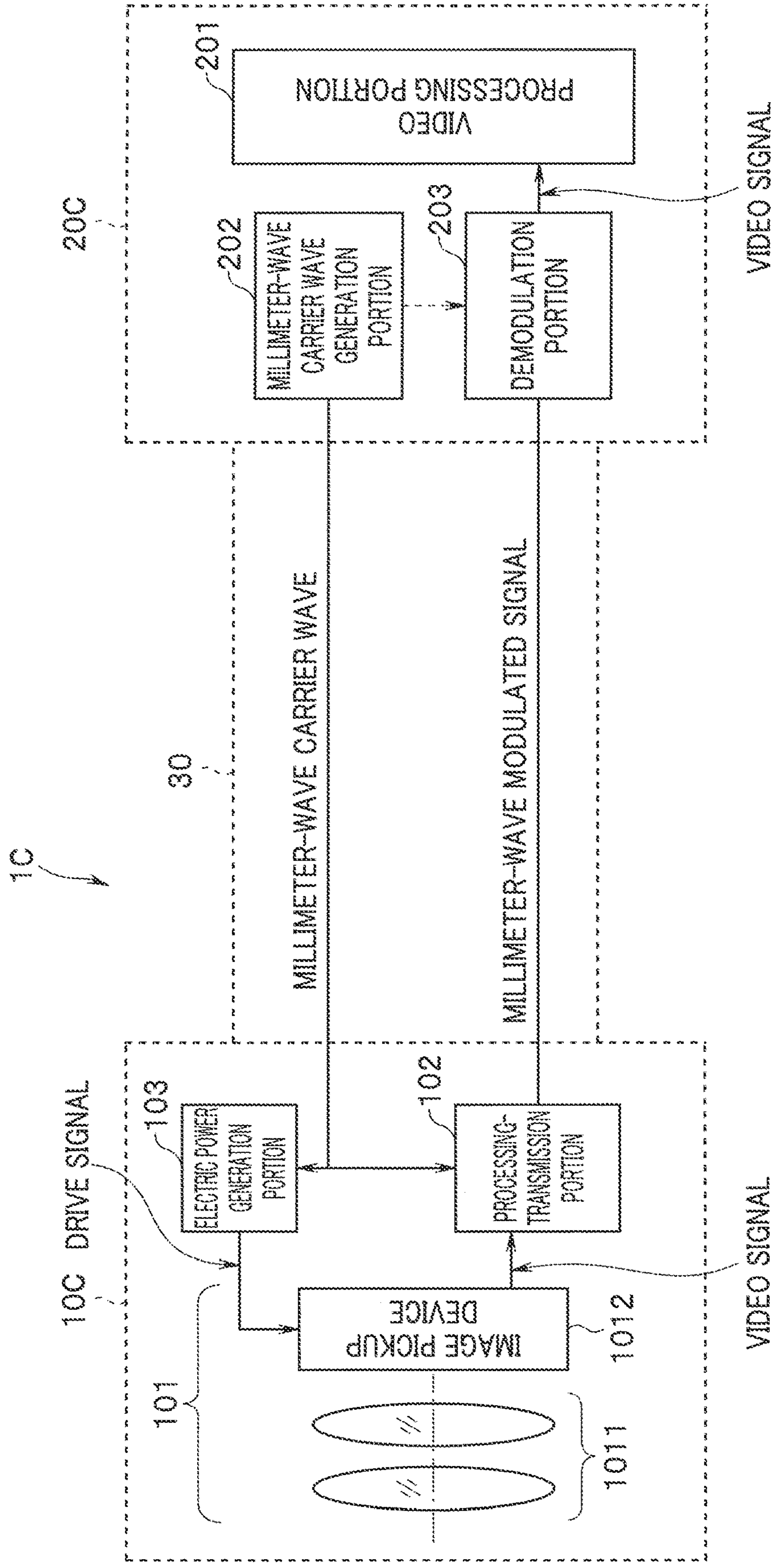
FIG. 8 is a block diagram illustrating a configuration of an image pickup apparatus of a third embodiment of the present invention.

FIG. 8 is a block diagram illustrating a configuration of the image pickup apparatus of the third embodiment of the present invention.

As illustrated in FIG. 8, an image pickup apparatus 1C of the third embodiment includes a second unit 20C having a configuration same as a configuration of the second unit 20A in the first embodiment, but a first unit 10C includes an electric power generation portion 103, which is a difference from the configuration of the first embodiment.

The electric power generation portion 103 in the third embodiment has a function to bifurcate and receive a part of a millimeter-wave carrier wave received by the first unit 10C through the waveguide path 30 and convert the part into electric power.

For example, an element typically called a rectenna may be used as a specific configuration of the electric power generation portion (electric power generation element) 103. The term rectenna means a rectifying antenna, which is an element configured to take out electric power by rectifying and converting a high-frequency signal received by an antenna into direct current.

The rectenna can be achieved with a simplest configuration in which a diode is disposed on a transmission line of the high-frequency signal, and electric power can be extracted from a millimeter-wave carrier wave with a simple and small-sized circuit. Note that the configuration of the electric power generation portion 103 is merely exemplary, and effects of the present invention can be obtained with any other configuration having a function to generate electric power from a millimeter-wave carrier wave.

In the third embodiment, electric power taken out from a millimeter-wave carrier wave by the electric power generation portion 103 can be used as electric power for driving the image pickup device 1012. Note that electric power for driving the image pickup device 1012 is needed in the first and second embodiments as well.

Specifically, in the first and second embodiments, electric power for driving the image pickup device is supplied with a configuration in which the electric power is supplied from the second unit to the first unit through a non-illustrated electric power line disposed in parallel to the waveguide path or a configuration in which a battery is provided in the first unit. This configuration is same in any following embodiment in which no electric power generation portion 103 is provided.

<Effects of Third Embodiment>

In addition to the effects of the first embodiment, the image pickup apparatus of the third embodiment can achieve configuration simplification and weight reduction of the image pickup apparatus. Specifically, the first embodiment, it is necessary that a non-illustrated electric power line is provided between the first unit and the second unit or a battery appropriate for electric power supply is provided in the first unit, but in the third embodiment, the electric power line and the battery do not need to be provided. Since the electric power line and the battery are unnecessary in this manner, configuration simplification and weight reduction of the image pickup apparatus can be achieved.

Fourth Embodiment

Subsequently, a fourth embodiment of the present invention will be described below.

An image pickup apparatus of the fourth embodiment has a main configuration same as in the first embodiment, but the first unit includes a clock generation portion, which is a difference from the first embodiment. Thus, only the difference from the first embodiment will be described below, and description of any common part is omitted.

Figure 9:
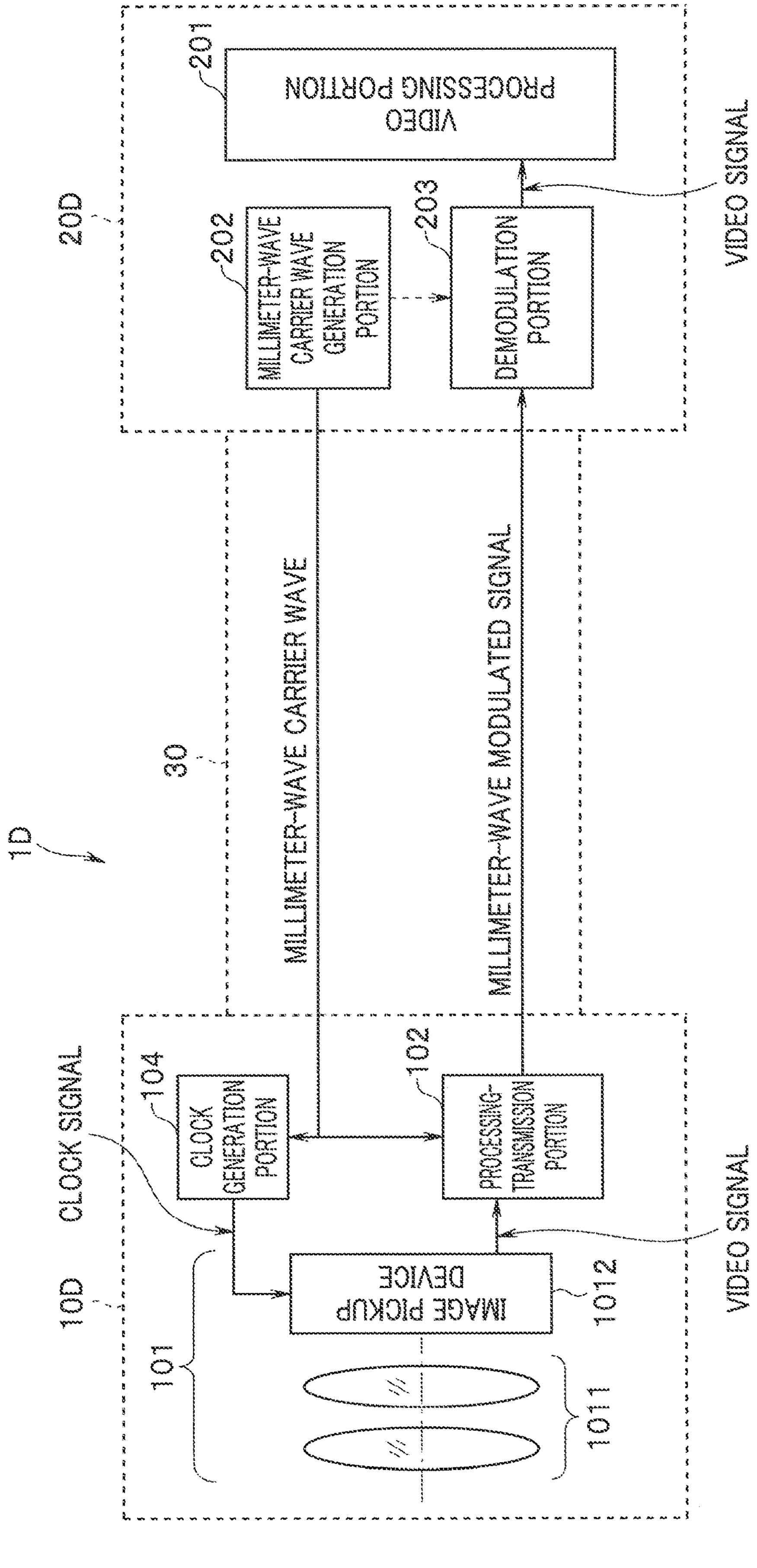
FIG. 9 is a block diagram illustrating a configuration of an image pickup apparatus of a fourth embodiment of the present invention.

FIG. 9 is a block diagram illustrating a configuration of the image pickup apparatus of the fourth embodiment of the present invention.

As illustrated in FIG. 9, an image pickup apparatus 1D of the fourth embodiment includes the second unit 20C having a configuration same as the configuration of the second unit 20A in the first embodiment, but the first unit 10C includes a clock generation portion 104, which is a difference from the configuration of the first embodiment.

The clock generation portion (clock generation circuit) 104 in the fourth embodiment has a function to generate, from a millimeter-wave carrier wave received by a first unit 10D through the waveguide path 30, a clock signal that is a reference signal necessary for drive of the image pickup device 1012.

A specific method by which the clock generation portion 104 generates the clock signal is, for example, a method with a frequency division circuit configured to generate a frequency suitable for the clock signal by dividing a frequency of the received millimeter-wave carrier wave (calculating 1/n (n is an integer) of the frequency of the electric wave).

In another method, the clock signal is superimposed, by using a non-illustrated mixer, on a millimeter-wave carrier wave generated by the millimeter-wave carrier wave generation portion 202 in a second unit 20D, and is then separated (detected) by the clock generation portion 104 and used.

Note that the above-described configuration is merely exemplary, and effects of the fourth embodiment can be obtained with a function to generate a clock signal by using a millimeter-wave carrier wave.

A clock signal generated from a millimeter-wave carrier wave by the clock generation portion 104 can be used as a reference signal that is necessary for operation of the image pickup device 1012. Note that the reference signal (clock signal) that is necessary for operation of the image pickup device 1012 is needed in the first, second, and third embodiments as well.

Specifically, in the first, second, and third embodiments, the reference signal that is necessary for operation of the image pickup device 1012 is supplied with a configuration in which the reference signal is supplied from the second unit to the first unit through a non-illustrated clock signal line disposed in parallel to the waveguide path 30 or a configuration in which a clock signal generation circuit is provided in the first unit. This configuration is same in any following embodiment in which no clock generation portion 104 is provided.

Note that an example in which a clock signal is superimposed on a millimeter-wave carrier wave is described above, and in such a case, disorder is likely to occur to the clock signal but can be corrected through relatively simple processing such as passing through LNAs as illustrated in FIGS. 5 and 6. Thus, use of a circuit for signal correction is a designing requirement, and the circuit is not limited to the configuration of the above-described embodiment but may be added as necessary in the present invention.

<Effects of Fourth Embodiment>

In addition to the effects of the first embodiment, the image pickup apparatus of the fourth embodiment can achieve configuration simplification and weight reduction of the image pickup apparatus. Specifically, in the first embodiment, it is needed that a non-illustrated clock line is provided between the first unit and the second unit or a circuit for generating the reference signal is provided in the first unit, but in the fourth embodiment, the clock line and the circuit for generating the reference signal do not need to be provided.

Specifically, according to the fourth embodiment, since the clock line and the circuit for generating the reference signal are unnecessary, simplification and weight reduction of the configuration of the image pickup apparatus can be achieved by, for example, simplifying a configuration of a line provided between the first unit and the second unit.

Note that the clock line typically needs to be a coaxial line for avoiding noise contamination, and this reduction improves manufacturability of the image pickup apparatus.

Fifth Embodiment

Subsequently, a fifth embodiment of the present invention will be described below.

An image pickup apparatus of the fifth embodiment has a main configuration same as in the first embodiment, but the first unit includes an image-pickup control signal reception-regeneration portion, which is a difference from the first embodiment. Thus, only the difference from the first embodiment will be described below, and description of any common part is omitted.

Figure 10:
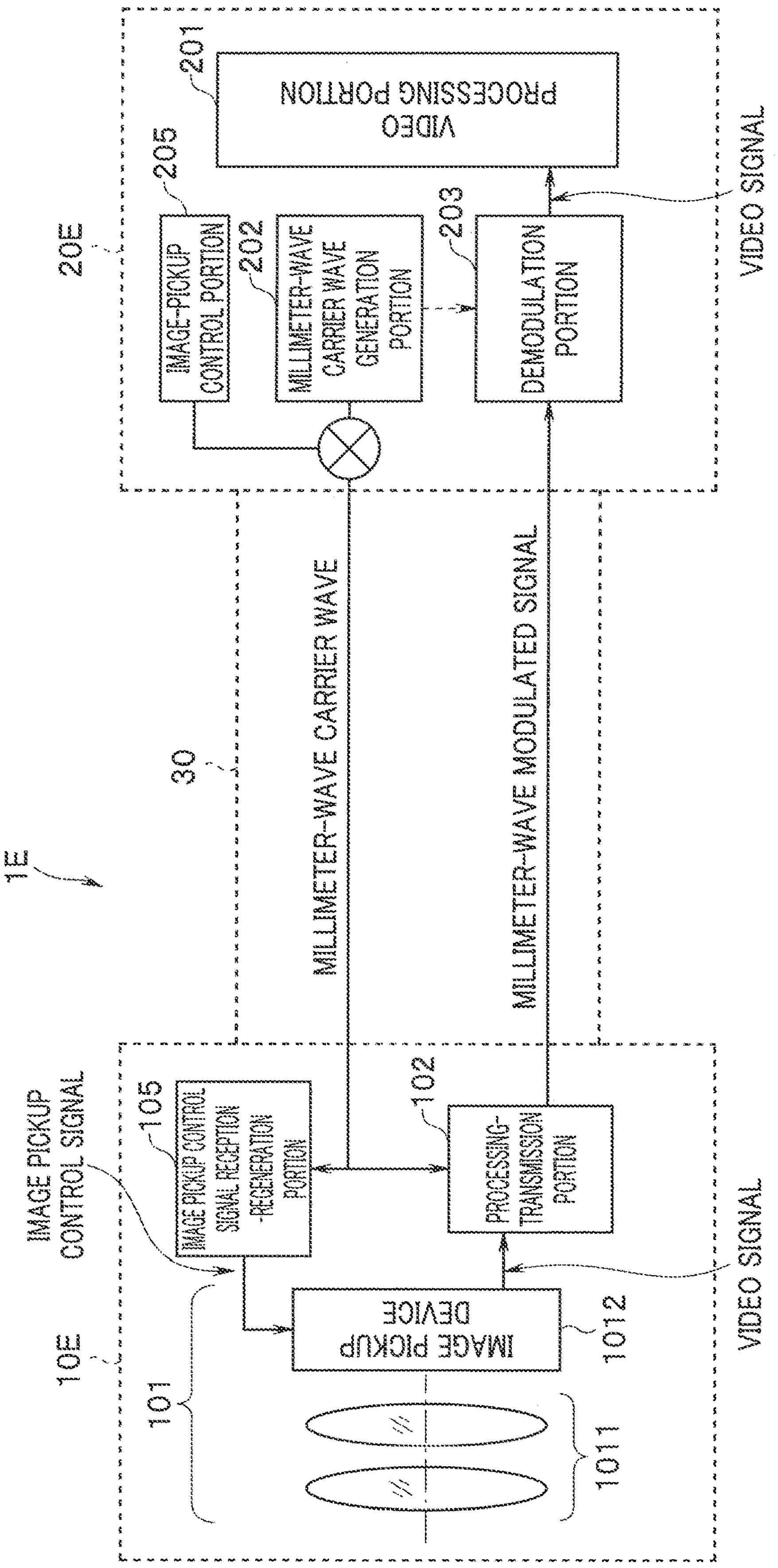
FIG. 10 is a block diagram illustrating a configuration of an image pickup apparatus of a fifth embodiment of the present invention.

FIG. 10 is a block diagram illustrating a configuration of the image pickup apparatus of the fifth embodiment of the present invention.

As illustrated in FIG. 10, in an image pickup apparatus 1E of the fifth embodiment, a first unit 10E includes an image-pickup control signal reception-regeneration portion 105 and a second unit 20E includes an image-pickup control portion 205, which is a difference from the configuration of the first embodiment.

The image-pickup control signal reception-regeneration portion (image-pickup control signal reception-regeneration circuit) 105 in the fifth embodiment receives an image-pickup control signal generated by the image-pickup control portion (image-pickup control circuit) 205 in the second unit 20E through the waveguide path 30 and regenerates the image-pickup control signal. The image-pickup control signal reception-regeneration portion 105 has a function to supply the received and regenerated image-pickup control signal to the image pickup device 1012.

The image-pickup control signal is generated by the image-pickup control portion 205 in the second unit 20E as described above, mixed with a millimeter-wave carrier wave generated by the millimeter-wave carrier wave generation portion 202, and sent to the waveguide path 30.

Note that although the image-pickup control portion 205 is newly explicitly described in the fifth embodiment, a site corresponding to the image-pickup control portion 205, which contributes to control of the image pickup device 1012, exists in the first to fourth embodiments as well, and a non-illustrated image pickup device is controlled, separately from the waveguide path 30, through a control signal line for controlling the image pickup device.

In the fifth embodiment, the image-pickup control signal is mixed with a millimeter-wave carrier wave and transmitted, but in another method, the image-pickup control signal may be transferred in a time-divisional manner.

The above-described configuration is merely exemplary, and effects of the fifth embodiment can be obtained with a function to receive and regenerate to the image-pickup control signal transmitted through the waveguide path 30.

<Effects of Fifth Embodiment>

In addition to the effects of the first embodiment, the image pickup apparatus of the fifth embodiment can achieve configuration simplification and weight reduction of the image pickup apparatus. Specifically, in the first embodiment, a non-illustrated image-pickup control signal line needs to be provided between the first unit and the second unit, but in the fifth embodiment, the image-pickup control signal line does not need to be provided.

Specifically, according to the fifth embodiment, since the image-pickup control signal line is unnecessary, simplification and weight reduction of the configuration of the image pickup apparatus can be achieved by simplifying a configuration of a line provided between the first unit and the second unit.

Sixth Embodiment

Subsequently, a sixth embodiment of the present invention will be described below.

An image pickup apparatus of the sixth embodiment has a main configuration same as in the first embodiment, but the first unit includes an electric power generation portion, a clock generation portion, and an image-pickup control signal reception-regeneration portion, which is a difference from the first embodiment. Thus, only the difference from the first embodiment will be described below, and description of any common part is omitted.

Figure 11:
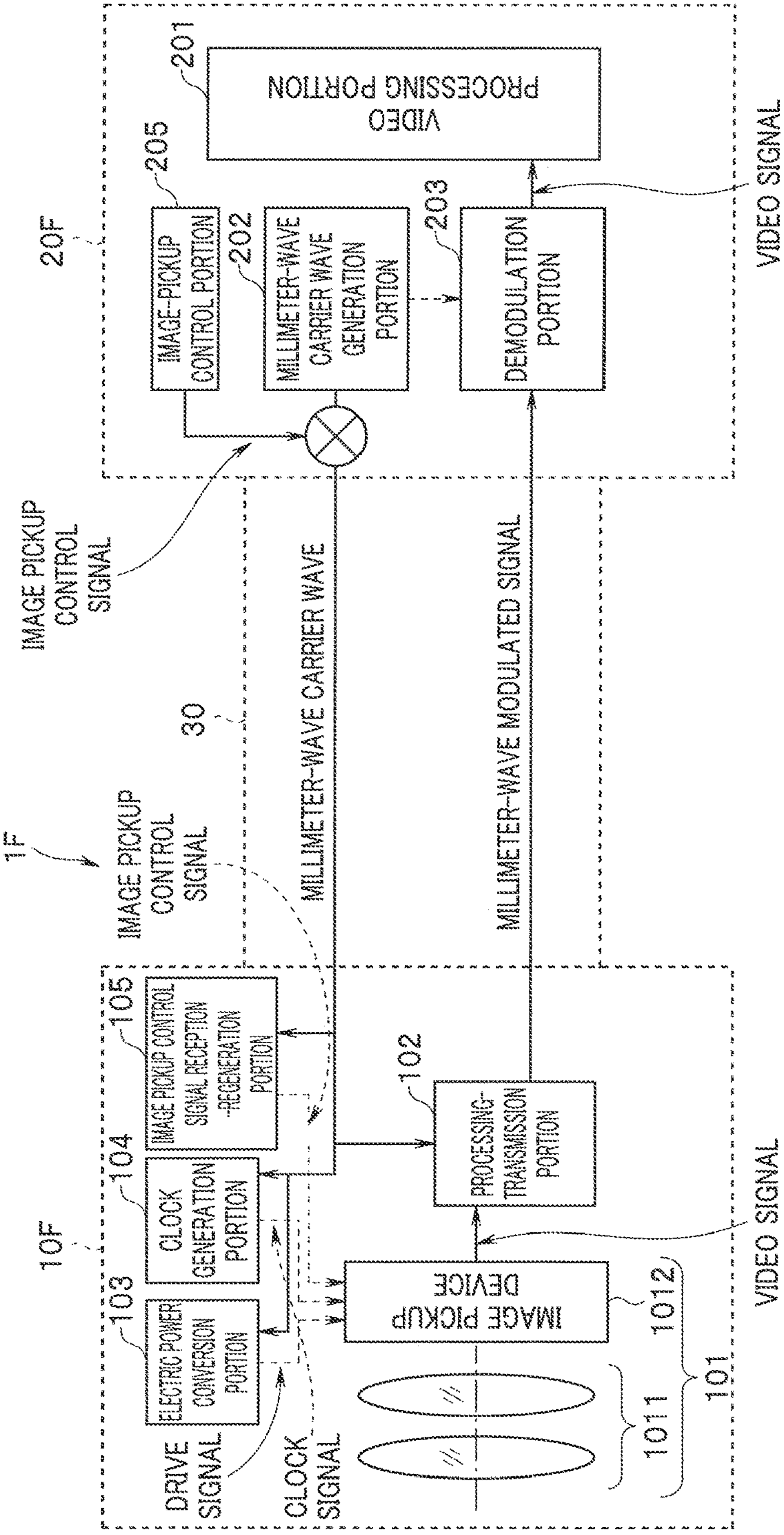
FIG. 11 is a block diagram illustrating a configuration of an image pickup apparatus of a sixth embodiment of the present invention.

FIG. 11 is a block diagram illustrating a configuration of the image pickup apparatus of the sixth embodiment of the present invention.

As illustrated in FIG. 11, in an image pickup apparatus 1F of the sixth embodiment, a first unit 10F includes the electric power generation portion 103 in the third embodiment, the clock generation portion 104 in the fourth embodiment, and the image-pickup control signal reception-regeneration portion 105 in the fifth embodiment, and a second unit 20F includes the image-pickup control portion 205, which is a difference from the configuration of the first embodiment.

Specifically, since the first unit includes the electric power generation portion 103 in the image pickup apparatus of the sixth embodiment, an electric power line for supplying electric power to the image pickup device 1012 and a battery in the first unit are unnecessary as described in the third embodiment.

Moreover, since the first unit includes the clock generation portion 104 in the image pickup apparatus of the sixth embodiment, a clock signal line for supplying the clock signal to the image pickup device 1012 and an oscillator in the first unit are unnecessary as described in the fourth embodiment.

Furthermore, since the first unit includes the image-pickup control signal reception-regeneration portion 105 in the image pickup apparatus of the sixth embodiment, an image-pickup control signal line for transferring an image-pickup control signal that is necessary for controlling the image pickup device 1012 is unnecessary as described in the fifth embodiment.

In addition, similarly to the first embodiment, the waveguide path 30 is configured as a waveguide pipe including the internal dielectric 301 extending with a uniform dielectric constant in the longitudinal direction and the outer conductor (metal layer) 302 covering the outer periphery of the dielectric continuously extending in the longitudinal direction, and thus the outer conductor 302 may be a GND line connecting the first unit 10F and the second unit 20F.

Accordingly, in the image pickup apparatus of the sixth embodiment, the drive electric power, the clock signal, the image-pickup control signal, and GND, which are necessary for operating the image pickup device 1012, can be all supplied through the waveguide path 30.

Note that, in the sixth embodiment, the image pickup device 1012, the clock generation portion 104, and the image-pickup control signal reception-regeneration portion 105 are integrated on the same silicon chip through the same CMOS process. In other words, the image pickup device 1012, the clock generation portion 104, and the image-pickup control signal reception-regeneration portion 105 are unified. The unification of these functions contributes to size reduction, manufacturability improvement, and operation stabilization, but a pattern of the unification is not limited to the above-described pattern.

<Effects of Sixth Embodiment>

In addition to the effects of the first embodiment, the image pickup apparatus of the sixth embodiment can achieve significant configuration simplification and weight reduction of the image pickup apparatus.

Specifically, according to the sixth embodiment, only the waveguide path 30 is a line connecting the first unit 10F and the second unit 20F. Accordingly, the number of connection lines decreases, and thus manufacturability can be significantly improved.

Moreover, according to the sixth embodiment, since the image pickup device 1012, the clock generation portion 104, and the image-pickup control signal reception-regeneration portion 105 are integrated (unified) on the same silicon chip through the same CMOS process, manufacturability can be improved and operation of the image pickup apparatus can be stabilized.

Seventh Embodiment

Subsequently, a seventh embodiment of the present invention will be described below.

The seventh embodiment of the present invention is characterized in that the image pickup apparatus of the first embodiment described above is applied to a camera including a shake correction mechanism configured to correct shake of an image pickup portion.

Figure 12:
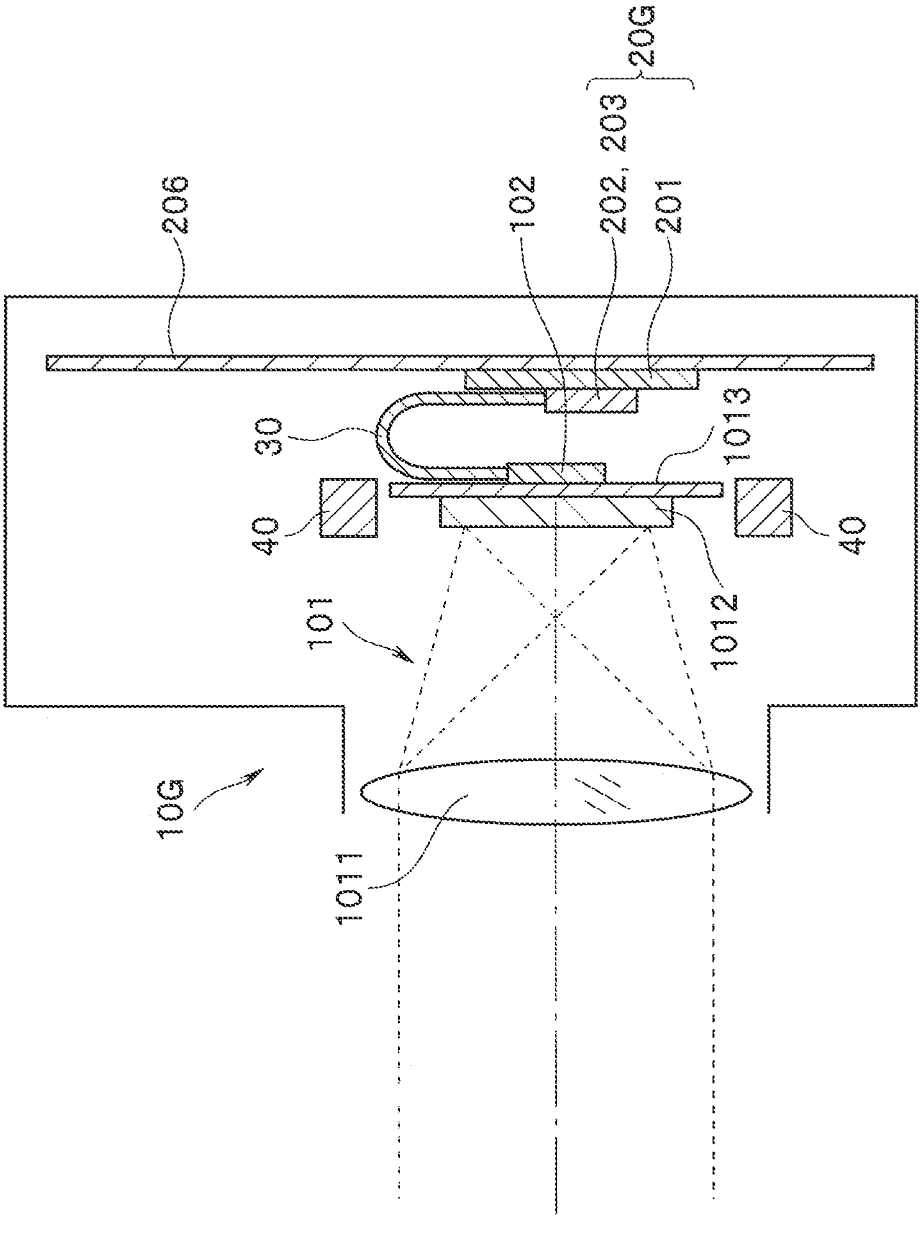
FIG. 12 is a diagram illustrating a configuration of a camera that is a seventh embodiment of the present invention and to which an image pickup apparatus is applied.

FIG. 12 is a diagram illustrating a configuration of the camera that is the seventh embodiment.

As illustrated in FIG. 12, the camera of the present embodiment includes a first unit 10G having a role same as a role of the first unit 10A in the first embodiment described above. The first unit 10G includes the image pickup portion 101 and the processing-transmission portion 102, which are same as in the first embodiment.

The image pickup portion 101 in the seventh embodiment includes the image pickup optical system 1011 on which a subject image is incident, and the image pickup device 1012. The image pickup device 1012 is mounted on an image pickup substrate 1013 and disposed on the back side of the image pickup optical system 1011, picks up the subject image, and outputs a predetermined video signal through photoelectric conversion.

In addition, a well-known image stabilization drive portion 40 configured to correct shake of the image pickup device 1012 is disposed on a side of the image pickup device 1012 in the image pickup portion 101 and corrects shake of the image pickup device 1012 as appropriate.

On the back side of the image pickup portion 101, the processing-transmission portion 102 having a role same as in the first embodiment is disposed on a back surface side of the image pickup substrate 1013.

Similarly to the first embodiment, the processing-transmission portion 102 receives a millimeter-wave carrier wave generated by a millimeter-wave carrier wave generation portion in the second unit 20G through the waveguide path 30 installed between the processing-transmission portion 102 and a second unit 20G to be described later, generates a millimeter-wave modulated wave (millimeter-wave modulated signal) by superimposing a video signal generated by the image pickup portion 101 on the millimeter-wave carrier wave, and transmits the millimeter-wave modulated signal toward the waveguide path 30.

The camera of the seventh embodiment includes the second unit 20G having a role same as a role of the second unit 20A in the first embodiment. The second unit 20G is disposed on the back side of the image pickup portion 101, and similarly to the first embodiment, includes the millimeter-wave carrier wave generation portion 202 configured to generate the millimeter-wave carrier wave, the demodulation portion 203 configured to acquire the video signal based on the millimeter-wave modulated signal on which the video signal is superimposed and that is outputted from the first unit 10G, and the video processing portion 201 configured to perform predetermined processing on the acquired video signal.

Note that the video processing portion 201, the millimeter-wave carrier wave generation portion 202, and the demodulation portion 203 are mounted on a predetermined main substrate 206.

In the seventh embodiment as well, the millimeter-wave carrier wave generation portion 202 includes a non-illustrated oscillation element or oscillation circuit. The millimeter-wave carrier wave generation portion 202 generates the millimeter-wave carrier wave based on a predetermined reference signal generated by the oscillation element or the oscillation circuit and outputs the millimeter-wave carrier wave. Specifically, the millimeter-wave carrier wave is generated by, for example, multiplying the reference signal.

The demodulation portion 203 receives the millimeter-wave modulated signal generated by the processing-transmission portion 102 in the first unit 10G through the waveguide path 30 and regenerates (restores) the video signal generated by the image pickup portion 101 by using a signal generated by the millimeter-wave carrier wave generation portion 202.

In the seventh embodiment, the waveguide path 30 is installed between the first unit 10G and the second unit 20G.

In the seventh embodiment as well, similarly to the first embodiment, the waveguide path 30 is configured as, for example, a flexible waveguide pipe, and specifically, configured as a waveguide pipe including the flexible internal dielectric 301 extending with a uniform dielectric constant in the longitudinal direction and the outer conductor 302 that is a flexible metal layer covering the outer periphery of the dielectric continuously extending in the longitudinal direction.

<Effects of Seventh Embodiment>

In the image pickup apparatus of the seventh embodiment, significant size and weight reduction of the first unit (image pickup unit) can be achieved, in particular, since the second unit (video processing unit) includes a generation portion (oscillation portion) configured to generate a reference signal from which a millimeter-wave carrier wave used for signal transmission is originated. Accordingly, operational performance of the shake correction drive portion 40 that corrects shake of the image pickup device 1012 can be improved.

Moreover, similarly to the first embodiment, a requirement for frequency stability of the reference signal can be significantly moderated to significantly reduce a circuit scale of a reference signal generation portion and appropriately transmit, for example, a video signal of a high-definition and large-volume video such as 4K or 8K.

Accordingly, a camera including an image pickup portion of a reduced size and a reduced weight, in particular, and capable of reliably transmitting a large-volume image pickup signal and accurately functioning a shake correction drive portion with a configuration of a small circuit scale can be obtained.

Note that the image pickup apparatus of the seventh embodiment is an application of the image pickup apparatus of the first embodiment described above to a camera including an image stabilization mechanism configured to correct shake of an image pickup portion, but the present embodiment is not limited to this configuration and may be an application of any of the image pickup apparatuses of the second to fifth embodiments described above.

Eighth Embodiment

Subsequently, an eighth embodiment of the present invention will be described below.

The eighth embodiment of the present invention is characterized in that the image pickup apparatus of the first embodiment (the image pickup apparatus 1A; refer to FIG. 1) described above is applied to an endoscope apparatus (endoscope system).

Figure 13:
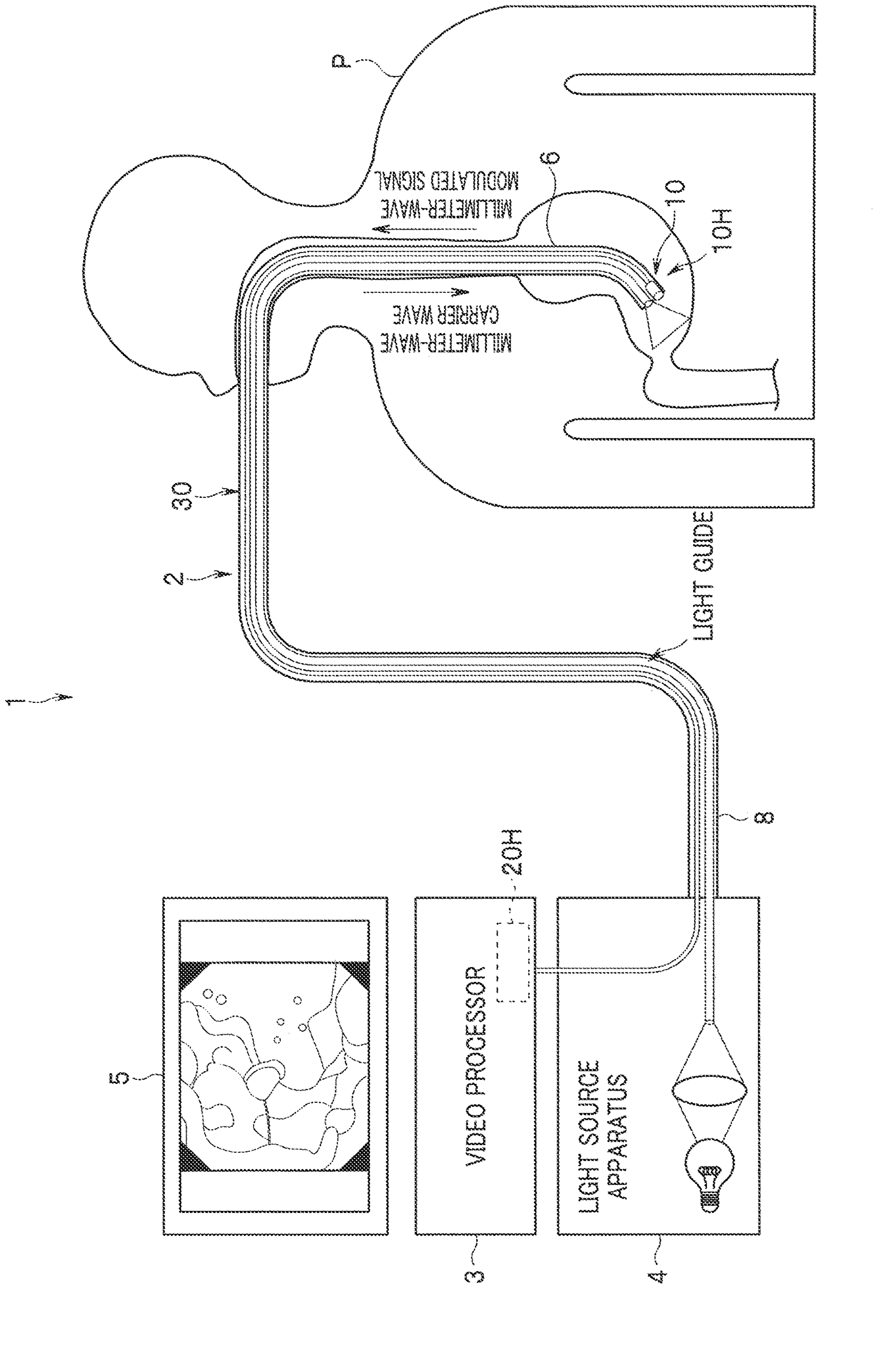
FIG. 13 is a block diagram illustrating a configuration of an endoscope apparatus that is an eighth embodiment of the present invention and to which an image pickup apparatus is applied.

FIG. 13 is a block diagram illustrating a configuration of the endoscope apparatus (endoscope system 1) that is the eighth embodiment of the present invention and to which the image pickup apparatus is applied.

As illustrated in FIG. 13, an endoscope apparatus (endoscope system) 1 is what is called an endoscope system for upper digestive tract. The endoscope system 1 mainly includes: an endoscope 2 including an image pickup portion configured to pick up a body cavity image of an object P with a distal end portion being inserted in a body cavity of a subject P and output an image signal of this object image; a video processor 3 including an image processing portion configured to perform predetermined image processing on the image signal outputted from the image pickup portion in the endoscope 2, the video processor 3 being configured to collectively control entire operation of the endoscope system 1; a light source apparatus 4 configured to generate illumination light to be emitted from a distal end of the endoscope 2; and a display apparatus 5 configured to display an image provided with image processing by the video processor 3.

The endoscope 2 includes an insertion portion 6 including the image pickup portion at a distal end portion and configured as a flexible elongated-shape portion, an operation portion connected on a base end side of the insertion portion 6 and configured to receive inputting of various operation signals, and a universal cord 8 extending from the operation portion toward the base end side and connected to the video processor 3 and the light source apparatus 4.

The insertion portion 6 includes a distal-end rigid portion 10 disposed at a most distal end portion and including, for example, the image pickup portion, a freely-bendable bending portion disposed on the base end side of the distal-end rigid portion 10 and formed of a plurality of bent pieces, and an elongated flexible tube portion connected on the base end side of the bending portion.

In the insertion portion 6, a first unit (image pickup unit) 10H including the image pickup portion configured to pick up an image of an object and generate a video signal is disposed at the distal-end rigid portion 10. The first unit 10H has functions same as functions of the first unit 10A in the first embodiment and includes the image pickup portion 101 and the processing-transmission portion 102 described above (refer to FIG. 1).

Specifically, in the endoscope system 1 according to the eighth embodiment as well, the image pickup portion 101 in the first unit 10H includes the image pickup optical system 1011 on which a subject image is incident and the image pickup device 1012. The image pickup device 1012 is disposed on the back side of the image pickup optical system 1011, picks up the subject image, and outputs a predetermined video signal through photoelectric conversion.

Note that the image pickup device 1012 in the present embodiment is, for example, a complementary metal oxide semiconductor (CMOS) image sensor including pixels in a number equal to or larger than two million pixels, which is the number of pixels corresponding to what is called full high definition or higher.

The video processor 3 has a function to collectively control entire operation of the endoscope system 1 and includes a second unit 2011 having functions same as functions of the second unit 20A in the first embodiment.

Similarly to the second unit 20A in the first embodiment, the second unit 20H includes the millimeter-wave carrier wave generation portion 202 configured to generate a millimeter-wave carrier wave, the demodulation portion 203 configured to acquire a video signal based on a millimeter-wave modulated signal on which the video signal outputted from the first unit 10H is superimposed, and the video processing portion 201 configured to perform predetermined processing on the acquired video signal.

The endoscope 2 also includes, between the image pickup portion 101 in the first unit 10H disposed at a distal end portion of the insertion portion 6 and the video processing portion 201 of the second unit 2011 in the video processor 3, a signal transmission path extending from the image pickup portion 101 to the video processing portion 201 of the video processor 3 through inside of the insertion portion 6, the operation portion, and the universal cord 8.

In the endoscope system according to the eighth embodiment, the signal transmission path is configured as the waveguide path 30, same as in the first embodiment, through which a millimeter wave or submillimeter wave (hereinafter representatively referred to as a millimeter wave in some cases) passes.

Note that, in the present embodiment, the universal cord 8 and the insertion portion 6 in the endoscope 2 include, together with the waveguide path 30 as the signal transmission path described above, a light guide for transmitting illumination light generated by the light source apparatus 4, a transmission means of electric power for driving the image pickup portion 101, a predetermined drive signal, or the like, as well as a well-known functional means such as a channel hole for allowing insertion of a non-illustrated predetermined treatment instrument or the like.

Subsequently, signal transmission of a millimeter-wave carrier signal and a millimeter-wave modulated signal transmitted through the waveguide path 30 in the endoscope system of the present embodiment will be described below.

In the endoscope system according to the eighth embodiment as well, similarly to the first embodiment, the millimeter-wave carrier wave generation portion 202 in the second unit 20H generates a millimeter-wave carrier wave based on a predetermined reference signal generated by a non-illustrated oscillation element or oscillation circuit, and outputs the millimeter-wave carrier wave toward the waveguide path 30. Specifically, the millimeter-wave carrier wave is generated by, for example, multiplying the reference signal.

The processing-transmission portion 102 in the first unit 10H receives the millimeter-wave carrier wave generated by the millimeter-wave carrier wave generation portion 202 in the second unit 20H through the waveguide path 30, generates a millimeter-wave modulated wave (millimeter-wave modulated signal) by superimposing the video signal generated by the image pickup portion 101 on the millimeter-wave carrier wave, and transmits the millimeter-wave modulated signal toward the waveguide path 30.

In addition, the demodulation portion 203 in the second unit 20H receives the millimeter-wave modulated signal generated by the processing-transmission portion 102 in the first unit 10H through the waveguide path 30, and regenerates (restores) the video signal generated by the image pickup portion 101 by using a signal generated by the millimeter-wave carrier wave generation portion 202.

<Waveguide Path 30 in Eighth Embodiment>

The waveguide path 30 in the endoscope system 1 of the eighth embodiment is configured as, for example, a flexible waveguide pipe as described above, and specifically, configured as a waveguide pipe including the flexible internal dielectric 301 extending with a uniform dielectric constant in the longitudinal direction, and the outer conductor 302 that is a flexible metal layer covering the outer periphery of the dielectric continuously extending in the longitudinal direction, as illustrated in FIGS. 2 to 4.

In the endoscope system 1 of the eighth embodiment as well, the waveguide path 30 is configured as, for example, a flexible waveguide pipe as described above and is a waveguide path that is a signal transmission path connecting the first unit 10H disposed at the distal end portion of the insertion portion of the endoscope and the second unit 20H disposed in the video processor 3 and through at least part of which a millimeter wave or a submillimeter wave propagates.

Specifically, the waveguide path 30 in the present embodiment newly provides, in place of a lead-wire signal transmission scheme or an optical-fiber signal transmission scheme that has been conventionally used, a signal transmission scheme using a waveguide path (flexible waveguide pipe) through which a millimeter wave or a submillimeter wave (electric wave having a frequency of 30 to 600 GHz approximately) passes as a signal transmission scheme for connecting the first unit 10H including the image pickup portion 101 disposed at the distal end portion of the insertion portion of the endoscope and the second unit 20H including the video processing portion of the video processor 3 connected to the endoscope.

<Effects of Eighth Embodiment>

In the endoscope system of the eighth embodiment, the waveguide path 30 is employed as a signal transmission scheme connecting the first unit 10H including the image pickup portion 101 disposed at the distal end portion of the insertion portion of the endoscope and the second unit 20H including the video processing portion of the video processor 3 connected to the endoscope, and a generation portion (oscillation portion) configured to generate a reference signal from which a millimeter-wave carrier wave used for signal transmission is originated is provided in the video processing portion on the video processor 3 side, and thus image transmission by a millimeter wave or a submillimeter wave (electric wave having a frequency of 30 to 600 GHz approximately) is enabled and significant size and weight reduction of the distal end portion of the insertion portion of the endoscope 2 can be achieved.

Moreover, a requirement for frequency stability of the reference signal can be significantly moderated to significantly reduce a circuit scale of a reference signal generation portion and appropriately transmit a high-speed image pickup signal. Accordingly, an image pickup apparatus (endoscope system) including an image pickup portion of a reduced size and a reduced weight, in particular, and capable of reliably transmitting a large-volume image pickup signal with a configuration of a small circuit scale can be obtained.

Note that the eighth embodiment is an application of the image pickup apparatus of the first embodiment described above to the endoscope apparatus (endoscope system), but the present embodiment is not limited to this configuration and may be an application of any of the image pickup apparatuses of the second to fifth embodiments described above.

Ninth Embodiment

Subsequently, a ninth embodiment of the present invention will be described below.

The ninth embodiment of the present invention is characterized in that the image pickup apparatus of the first embodiment (the image pickup apparatus 1A; refer to FIG. 1) described above is applied to an unmanned flying body (mobile body) referred to as a drone.

Figure 14:
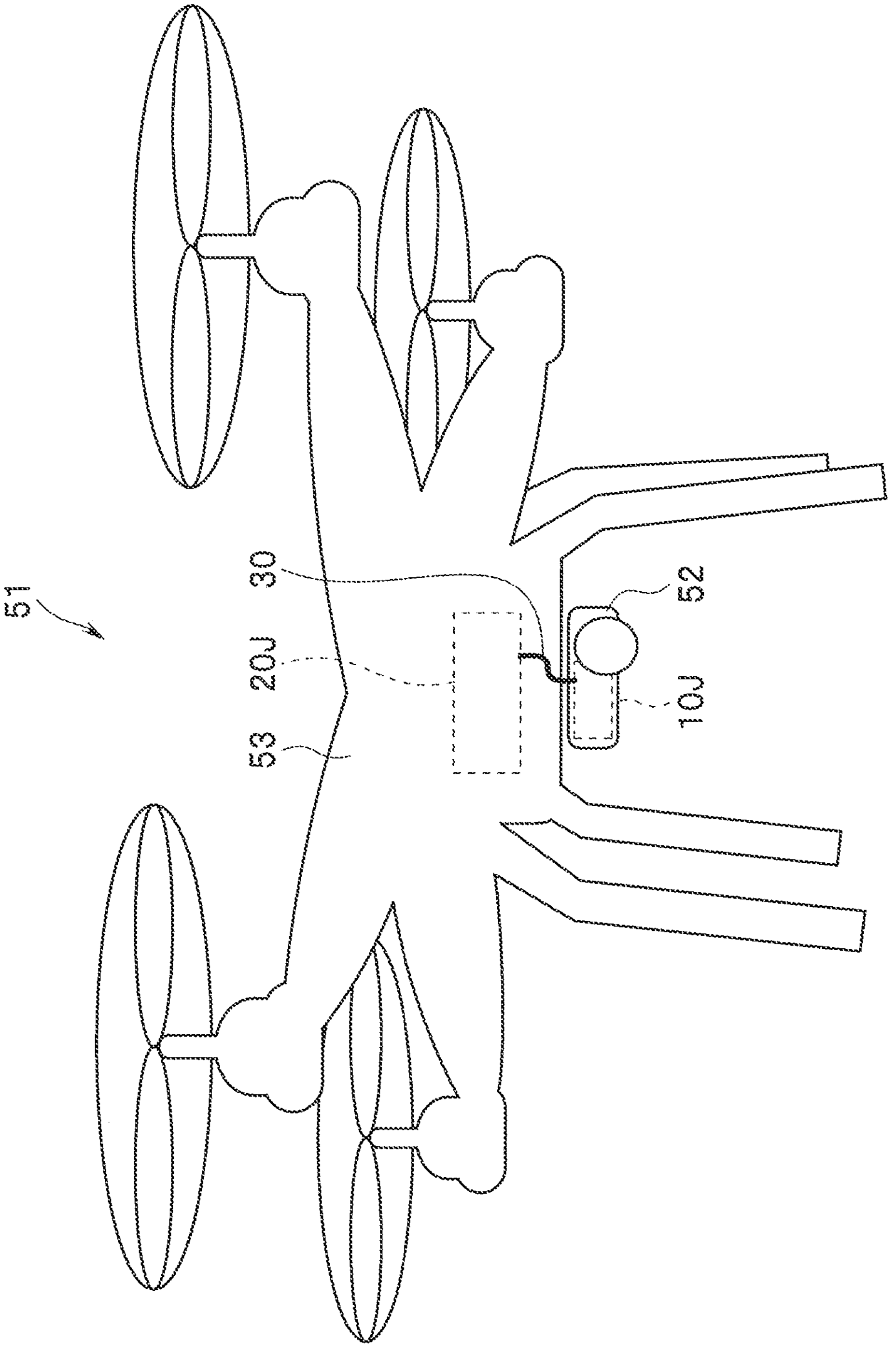
FIG. 14 is a schematic exterior diagram illustrating a configuration of a mobile body (drone) that is a ninth embodiment of the present invention and to which an image pickup apparatus is applied.

FIG. 14 is a block diagram illustrating a configuration of the drone (mobile body) that is the ninth embodiment of the present invention and to which the image pickup apparatus is applied.

As illustrated in FIG. 14, a drone 51 is a small-sized unmanned flying body configured to perform flying by remote control or autonomous flying based on a GPS or the like, and flies by receiving an instruction signal from, for example, a remote controller on a ground or GPS signals.

The drone 51 in the present embodiment includes, in addition to various mechanism portions (such as a well-known propeller) for flying, a drone control portion 53, a camera 52 mounted on a drone body, and the waveguide path 30 connecting the camera 52 and the drone control portion 53.

The drone control portion 53 includes a body control portion configured to control the entire drone, a flying control portion configured to perform, for example, motor drive control of a propeller under control of the body control portion, and well-known components including various sensors such as a gyro and a power source. The drone control portion 53 in the present embodiment also includes a second unit 20J having functions same as the functions of the second unit 20A in the first embodiment.

The camera 52 includes a first unit (image pickup unit) 10J controlled by the body control portion and including an image pickup portion configured to pick up an image of an object and generate a video signal. The first unit 10J has functions same as the functions of the first unit 10A in the first embodiment and includes the image pickup portion 101 and the processing-transmission portion 102 described above (refer to FIG. 1).

Specifically, in the drone 51 according to the ninth embodiment as well, the image pickup portion 101 in the first unit 10J includes the image pickup optical system 1011 on which an object image is incident and the image pickup device 1012. The image pickup device 1012 is disposed on the back side of the image pickup optical system 1011, picks up a subject image through photoelectric conversion, and outputs a predetermined video signal.

Note that the image pickup device 1012 in the present embodiment is, for example, a complementary metal oxide semiconductor (CMOS) image sensor including pixels in a number equal to or larger than two million pixels, which is the number of pixels corresponding to what is called full high definition or higher.

As described above, the drone control portion 53 in the present embodiment includes the second unit 20J having functions same as the functions of the second unit 20A in the first embodiment. Similarly to the second unit 20A in the first embodiment, the second unit 20J includes the millimeter-wave carrier wave generation portion 202 configured to generate a millimeter-wave carrier wave, the demodulation portion 203 configured to acquire a video signal based on a millimeter-wave modulated signal on which the video signal outputted from the first unit 10H is superimposed, and the video processing portion 201 configured to perform predetermined processing on the acquired video signal.

The drone 51 also includes, between the image pickup portion 101 of the first unit 10J disposed in the camera 52 mounted on the drone body and the video processing portion 201 of the second unit 20J in the drone control portion 53, a signal transmission path extending from the image pickup portion 101 to the video processing portion 201.

In the drone 51 according to the ninth embodiment, the signal transmission path is configured as the waveguide path 30, same as in the first embodiment, through which a millimeter wave or a submillimeter wave (hereinafter representatively referred to as a millimeter wave in some cases) passes.

Note that, in the drone 51 of the present embodiment, a line having various functions to communicate a signal for driving the camera and the like may be disposed between the drone control portion 53 and the camera 52 together with the waveguide path 30 as the signal transmission path described above.

In the drone 51 according to the ninth embodiment as well, similarly to the first embodiment, the millimeter-wave carrier wave generation portion 202 in the second unit 20J generates a millimeter-wave carrier wave based on a predetermined reference signal generated by a non-illustrated oscillation element or oscillation circuit, and outputs the millimeter-wave carrier wave toward the waveguide path 30. Specifically, the millimeter-wave carrier wave is generated by, for example, multiplying the reference signal.

The processing-transmission portion 102 in the first unit 10J receives the millimeter-wave carrier wave generated by the millimeter-wave carrier wave generation portion 202 in the second unit 20J through the waveguide path 30, generates a millimeter-wave modulated wave (millimeter-wave modulated signal) by superimposing the video signal generated by the image pickup portion 101 on the millimeter-wave carrier wave, and transmits the millimeter-wave modulated signal toward the waveguide path 30.

In addition, the demodulation portion 203 in the second unit 20J receives the millimeter-wave modulated signal generated by the processing-transmission portion 102 in the first unit 10J through the waveguide path 30, and regenerates (restores) the video signal generated by the image pickup portion 101 by using a signal generated by the millimeter-wave carrier wave generation portion 202.

<Waveguide Path 30 in Ninth Embodiment>

In the drone 51 of the ninth embodiment, the waveguide path 30 is configured as, for example, a flexible waveguide pipe as described above, and specifically, configured as a waveguide pipe including the flexible internal dielectric 301 extending with a uniform dielectric constant in the longitudinal direction, and the outer conductor 302 that is a flexible metal layer covering the outer periphery of the dielectric continuously extending in the longitudinal direction, as illustrated in FIGS. 2 to 4.

In the drone 51 of the ninth embodiment as well, the waveguide path 30 is configured as, for example, a flexible waveguide pipe as described above and is a waveguide path that is a signal transmission path connecting the first unit 10J disposed in the camera 52 and the second unit 20J disposed in the drone control portion 53 and through at least part of which a millimeter wave or a submillimeter wave propagates.

Specifically, the waveguide path 30 in the present embodiment newly provides, in place of a lead-wire signal transmission scheme that has been conventionally used, a signal transmission scheme using a waveguide path (flexible waveguide pipe) through which a millimeter wave or a submillimeter wave (electric wave having a frequency of 30 to 600 GHz approximately) passes as a signal transmission scheme connecting the first unit 10J including the image pickup portion 101 disposed in the camera mounted on the drone and the second unit 20J including the video processing portion in the drone control portion 53 connected to the camera.

<Effects of Ninth Embodiment>

In the drone 51 of the ninth embodiment, the waveguide path 30 is employed as a signal transmission scheme connecting the first unit 10J including the image pickup portion 101 disposed in the camera 52 and the second unit 20J including the video processing portion in the drone control portion 53 connected to the camera, and a generation portion (oscillation portion) configured to generate a reference signal from which a millimeter-wave carrier wave used for signal transmission is originated is provided in the video processing portion on the drone control portion 53 side, and thus image transmission by a millimeter wave or a submillimeter wave (electric wave having a frequency of 30 to 600 GHz approximately) is enabled and significant size and weight reduction of the camera mounted on the drone can be achieved.

Moreover, a requirement for frequency stability of the reference signal can be significantly moderated to significantly reduce a circuit scale of a reference signal generation portion and appropriately transmit a high-speed image pickup signal. Accordingly, an image pickup apparatus (drone image pickup system) including an image pickup portion of a reduced size and a reduced weight, in particular, and capable of reliably transmitting a large-volume image pickup signal with a configuration of a small circuit scale can be obtained.

Note that effects of the mobile body as described in the ninth embodiment are not limited to the drone in the ninth embodiment but can be widely obtained with mobile bodies such as an automobile and an aircraft. Specifically, for any mobile body on which a camera can be mounted, significant camera size and weight reduction described in the present embodiment and appropriate high-speed transmission of an image pickup signal have an effect of increasing a value of a product.

Note that the ninth embodiment is an application of the image pickup apparatus of the first embodiment described above to an unmanned flying body (mobile body) referred to as a drone, but the present embodiment is not limited to this configuration and may be an application of any of the image pickup apparatuses of the second to fifth embodiments described above.

Tenth Embodiment

Subsequently, a tenth embodiment of the present invention will be described below.

The tenth embodiment of the present invention is characterized in that the image pickup apparatus of the first embodiment (the image pickup apparatus 1A; refer to FIG. 1) described above is applied to a camera-mounted automobile that is a mobile body, and in particular, a plurality of first units each including the image pickup portion 101 are mounted.

Figure 15:
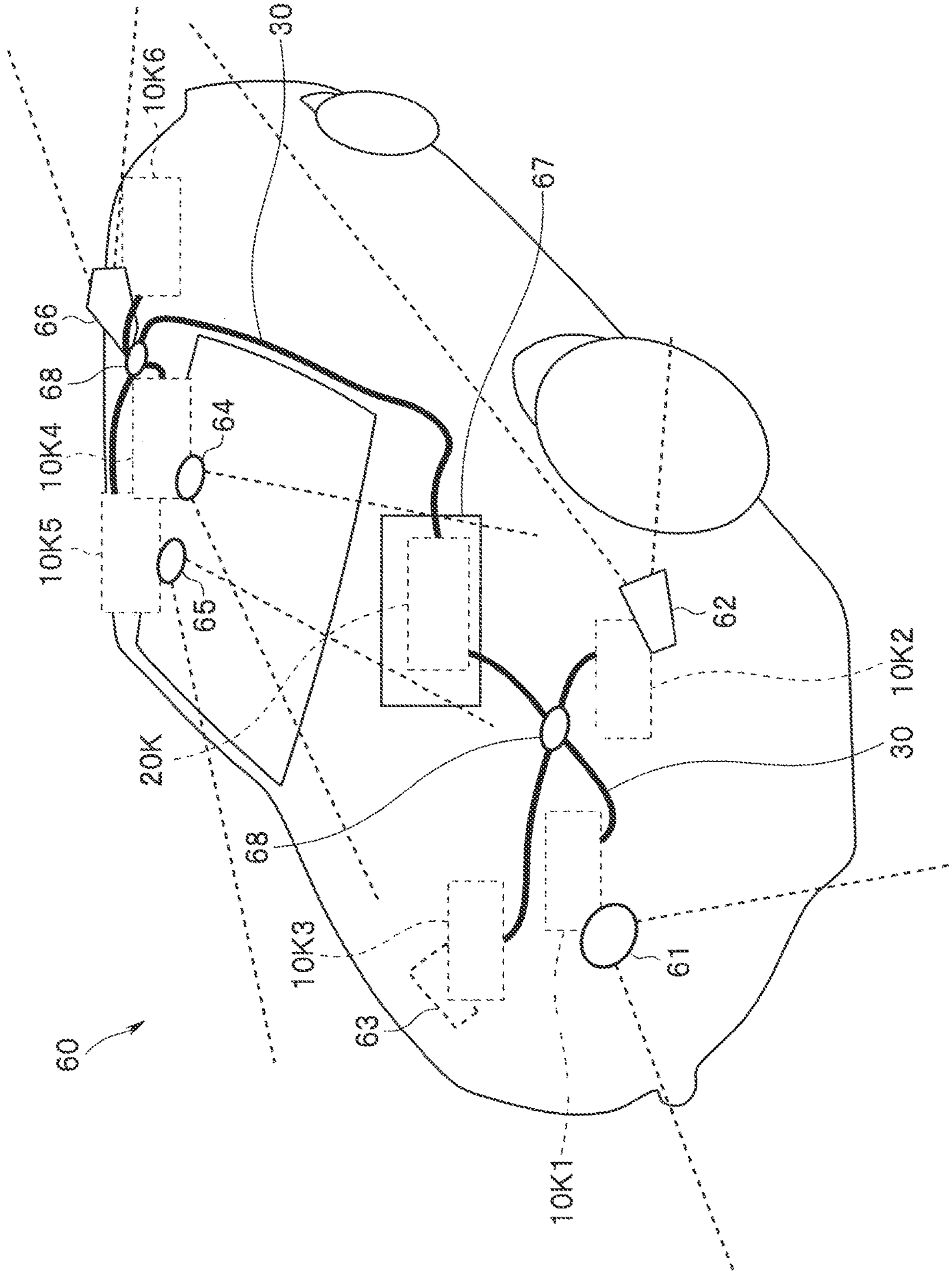
FIG. 15 is a schematic exterior diagram illustrating a configuration of a mobile body (camera-mounted automobile) that is a tenth embodiment of the present invention and to which an image pickup apparatus is applied.

FIG. 15 is a block diagram illustrating a configuration of the mobile body (camera-mounted automobile) that is the tenth embodiment of the present invention and to which the image pickup apparatus is applied.

As illustrated in FIG. 15, a camera-mounted automobile (hereinafter simply referred to as an automobile) 60 in the present embodiment includes, in addition to various mechanism portions for traveling, a plurality of monitoring cameras 61 to 66, a central electronic control unit 67, and the waveguide path 30 connecting the monitoring cameras 61 to 66 and the central electronic control unit 67.

The monitoring camera 61 is a near-front monitoring camera configured to monitor a front side near a vehicle, in particular, the monitoring cameras 62 and 63 are side-rear monitoring cameras configured to monitor a rear side from sides like door mirrors, the monitoring cameras 64 and 65 are front 3D cameras configured to stereoscopically monitor the front side, and the monitoring camera 66 is a rear camera configured to monitor the rear side.

The central electronic control unit 67 collectively controls entire operation of the automobile through overall control of information communication among various electronic control units (ECUs) such as an engine control ECU, a transmission control ECU, a charging control ECU, and a start-stop control ECU. For the central electronic control unit 67, the monitoring cameras 61 to 66 serve as sensors for performing various kinds of control.

The monitoring cameras 61 to 66 include first units (image pickup units) 10K1 to 10K6 controlled by the central electronic control unit 67 and each including an image pickup portion configured to pick up an image of surroundings of the automobile 60 and generate a video signal. The first units 10K1 to 10K6 have functions same as the functions of the first unit 10A in the first embodiment and each include the image pickup portion 101 and the processing-transmission portion 102 described above (refer to FIG. 1).

Specifically, in the automobile 60 according to the tenth embodiment as well, the image pickup portion 101 in each of the first units 10K1 to 10K6 includes the image pickup optical system 1011 on which an object image is incident and the image pickup device 1012. The image pickup device 1012 is disposed on the back side of the image pickup optical system 1011, picks up a subject image, and outputs a predetermined video signal through photoelectric conversion.

Note that the image pickup device 1012 in the present embodiment is, for example, a complementary metal oxide semiconductor (CMOS) image sensor including pixels in a number equal to or larger than two million pixels, which is the number of pixels corresponding to what is called full high definition or higher.

As described above, the central electronic control unit 67 in the present embodiment includes a second unit 20K having functions same as the functions of the second unit 20A in the first embodiment. Similarly to the second unit 20A in the first embodiment, the second unit 20K includes the millimeter-wave carrier wave generation portion 202 configured to generate a millimeter-wave carrier wave, the demodulation portion 203 configured to acquire a video signal based on a millimeter-wave modulated signal on which the video signal outputted from each of the first units 10K1 to 10K6 is superimposed, and the video processing portion 201 configured to perform predetermined processing on the acquired video signal.

The automobile 60 also includes, between the image pickup portion 101 in each of the first units 10K1 to 10K6 disposed in the monitoring cameras 61 to 66 and the video processing portion 201 in the second unit 20K in the central electronic control unit 67, a signal transmission path extending from the image pickup portion 101 to the video processing portion 201.

In the automobile 60 according to the tenth embodiment, the signal transmission path is configured as the waveguide path 30, same as in the first embodiment, through which a millimeter wave or a submillimeter wave (hereinafter representatively referred to as a millimeter wave in some cases) passes. Note that although the waveguide path 30 extends from the image pickup portion 101 to the video processing portion 201 as described above, a bifurcation point 68 is provided halfway through the signal transmission path as illustrated in FIG. 15 to bifurcate signals, thereby shortening a distance by which the waveguide path 30 is installed.

The bifurcation point 68 can be achieved by combining structures that each bifurcate the waveguide path 30 into a T shape. In the bifurcation, necessary connection capability can be adjusted by combining known members such as a circulator, an isolator, and a frequency filter as necessary.

In the automobile 60 of the present embodiment, a line having various functions to communicate signals for driving the monitoring cameras and the like may be disposed between the central electronic control unit 67 and the monitoring cameras 61 to 66 together with the waveguide path 30 as the signal transmission path described above. Although the bifurcation point 68 is provided on the signal transmission path, no bifurcation point 68 may be provided and the waveguide path 30 may directly connect the central electronic control unit 67 and each of the monitoring cameras 61 to 66.

In the automobile 60 according to the tenth embodiment as well, similarly to the first embodiment, the millimeter-wave carrier wave generation portion 202 in the second unit 20K generates a millimeter-wave carrier wave based on a predetermined reference signal generated by a non-illustrated oscillation element or oscillation circuit, and outputs the millimeter-wave carrier wave toward the waveguide path 30. Specifically, the millimeter-wave carrier wave is generated by, for example, multiplying the reference signal.

The processing-transmission portion 102 in each of the first units 10K1 to 10K6 receives the millimeter-wave carrier wave generated by the millimeter-wave carrier wave generation portion 202 in the second unit 20J through the waveguide path 30, generates a millimeter-wave modulated wave (millimeter-wave modulated signal) by superimposing the video signal generated by the image pickup portion 101 on the millimeter-wave carrier wave, and transmits the millimeter-wave modulated signal toward the waveguide path 30.

In addition, the demodulation portion 203 in the second unit 20K receives the millimeter-wave modulated signal generated by the processing-transmission portion 102 in each of the first units 10K1 to 10K6 through the waveguide path 30, and regenerates (restores) the video signal generated by the image pickup portion 101 by using a signal generated by the millimeter-wave carrier wave generation portion 202.

<Waveguide Path 30 in Tenth Embodiment>

In the automobile 60 of the tenth embodiment, the waveguide path 30 is configured as, for example, a flexible waveguide pipe as described above, and specifically, configured as a waveguide pipe including the flexible internal dielectric 301 extending with a uniform dielectric constant in the longitudinal direction and the outer conductor 302 that is a flexible metal layer covering the outer periphery of the dielectric continuously extending in the longitudinal direction, as illustrated in FIGS. 2 to 4.

In the automobile 60 of the tenth embodiment as well, the waveguide path 30 is configured as, for example, a flexible waveguide pipe as described above and is a waveguide path that is a signal transmission path connecting each of the first units 10K1 to 10K6 disposed in the monitoring cameras 61 to 66 and the second unit 20K disposed in the central electronic control unit 67 and through at least part of which a millimeter wave or a submillimeter wave propagates.

Specifically, the waveguide path 30 in the present embodiment newly provides, in place of a lead-wire signal transmission scheme that has been conventionally used, a signal transmission scheme using a waveguide path (flexible waveguide pipe) through which a millimeter wave or a submillimeter wave (electric wave having a frequency of 30 to 600 GHz approximately) passes as a signal transmission scheme connecting each of the first units 10K1 to 10K6 including the image pickup portions 101 disposed in the monitoring cameras mounted on the automobile and the second unit 20K including the video processing portion in the central electronic control unit 67 connected to the cameras.

<Effects of Tenth Embodiment>

With the automobile 60 of the tenth embodiment, it is possible to further increase an effect of achieving significant camera size and weight reduction and appropriate high-speed transmission of an image pickup signal, which are described in the ninth embodiment. Specifically, despite ever increasing importance of high-definition video transmission, such as action toward achievement of automated driving, and an increase of the number of image pickup units used per automobile, not each of a plurality of image pickup units needs to include a generation portion (oscillation portion) configured to generate a reference signal from which a millimeter-wave carrier wave used for signal transmission is originated, because the reference-signal generation portion (oscillation portion) is provided in common in the video processing portion on the central electronic control unit 67 side, which contributes to reduction of size and weight per automobile.

Note that the tenth embodiment is an application of the image pickup apparatus of the first embodiment described above to a camera-mounted automobile as a mobile body, but the present embodiment is not limited to this configuration and may be an application of any of the image pickup apparatuses of the second to fifth embodiments described above.

According to the present invention, it is possible to provide a more usable image pickup apparatus, an endoscope apparatus including the image pickup apparatus, a mobile body including the image pickup apparatus, an image pickup unit, and a video processing unit by achieving size and weight reduction of a unit including an image pickup device, a long transmission distance, and a high communication speed and moderating a high frequency-stability requirement for an oscillation circuit of a millimeter-wave communication system.

The present invention is not limited to the above-described embodiments but includes various kinds of changes, modifications, and the like without departing from the gist of the present invention.

What is claimed is:

1. An image pickup apparatus comprising:
- a first unit including an image pickup device configured to pick up an image of an object and generate a video signal;
- a second unit including a video processing circuit configured to perform predetermined processing on the video signal;
- a waveguide path that is provided between the first unit and the second unit and through which a millimeter wave or a submillimeter wave is transmitted;
- a millimeter-wave carrier-wave generation circuit disposed in the second unit and configured to generate a millimeter-wave carrier wave based on a predetermined reference signal;
- a processing-transmission circuit disposed in the first unit and configured to receive the millimeter-wave carrier wave generated by the millimeter-wave carrier-wave generation circuit in the second unit through the waveguide path, generate a millimeter-wave modulated wave by superimposing the video signal generated by the image pickup device on the millimeter-wave carrier wave, and transmit the millimeter-wave modulated wave toward the waveguide path; and
- a demodulator disposed in the second unit and configured to receive the millimeter-wave modulated wave generated in the first unit through the waveguide path and regenerate the video signal generated by the image pickup device, wherein:
- the second unit further includes a delay circuit disposed between the millimeter-wave carrier-wave generation circuit and the demodulator, and
- the delay circuit is set to provide, to a signal passing through the delay circuit, a delay time period equivalent to a round-trip signal transfer time period through the waveguide path.

2. The image pickup apparatus according to claim 1, wherein the first unit further includes an electric power generation element configured to generate, from part of the millimeter-wave carrier wave received through the waveguide path, electric power for driving the image pickup device and supply the electric power to the image pickup device.

3. The image pickup apparatus according to claim 1, wherein the first unit further includes a clock generation circuit configured to generate a clock signal that is an operation reference signal in the first unit from part of the millimeter-wave carrier wave received through the waveguide path and supply the clock signal to the image pickup device.

4. The image pickup apparatus according to claim 1, wherein:
- the second unit further includes an image-pickup control circuit configured to generate a predetermined image-pickup control signal, and
- the first unit further includes an image-pickup control signal reception-regeneration circuit configured to receive the image-pickup control signal generated by the image-pickup control circuit through the waveguide path, regenerate the image-pickup control signal, and supply the regenerated image-pickup control signal to the image pickup device.

5. The image pickup apparatus according to claim 1, wherein:
- the waveguide path includes:
  - a linear dielectric having a uniform dielectric constant in a longitudinal direction and having a section of a constant shape in the longitudinal direction, and
  - an outer conductor disposed at a position where the outer conductor covers an outer periphery of the dielectric, and
- the waveguide path is configured as a waveguide pipe that conducts an electric wave in a frequency band equal to or higher than a millimeter wave or a submillimeter wave near 60 GHz or higher.

6. The image pickup apparatus according to claim 5, wherein the outer conductor of the waveguide pipe is formed by twining, in a braided cord shape, flat foiled yarns containing a composite material of metal and resin.

7. The image pickup apparatus according to claim 1, wherein the processing-transmission circuit includes a modulator of on-off keying (OOK) or amplitude shift keying (ASK).

8. The image pickup apparatus according to claim 1, wherein the processing-transmission circuit includes a modulator of quadrature amplitude modulation (QAM).

9. The image pickup apparatus according to claim 1, wherein the first unit further includes an image stabilization mechanism configured to correct shake of the image pickup device.

10. An endoscope apparatus comprising an image pickup apparatus including:

a first unit including an image pickup device configured to pick up an image of an object and generate a video signal;

a second unit including a video processing circuit configured to perform predetermined processing on the video signal;

a waveguide path that is provided between the first unit and the second unit and through which a millimeter wave or a submillimeter wave is transmitted;

a millimeter-wave carrier-wave generation circuit disposed in the second unit and configured to generate a millimeter-wave carrier wave based on a predetermined reference signal;

a processing-transmission circuit disposed in the first unit and configured to receive the millimeter-wave carrier wave generated by the millimeter-wave carrier-wave generation circuit in the second unit through the waveguide path, generate a millimeter-wave modulated wave by superimposing the video signal generated by the image pickup device on the millimeter-wave carrier wave, and transmit the millimeter-wave modulated wave toward the waveguide path; and a demodulator disposed in the second unit and configured to receive the millimeter-wave modulated wave generated in the first unit through the waveguide path and regenerate the video signal generated by the image pickup device, wherein:

the second unit further includes a delay circuit disposed between the millimeter-wave carrier-wave generation circuit and the demodulator, and the delay circuit is set to provide, to a signal passing through the delay circuit, a delay time period equivalent to a round-trip signal transfer time period through the waveguide path.

11. A mobile body including an image pickup apparatus comprising:

a first unit including an image pickup device configured to pick up an image of an object and generate a video signal;

a second unit including a video processing circuit configured to perform predetermined processing on the video signal;

a waveguide path that is provided between the first unit and the second unit and through which a millimeter wave or a submillimeter wave is transmitted;

a millimeter-wave carrier-wave generation circuit disposed in the second unit and configured to generate a millimeter-wave carrier wave based on a predetermined reference signal;

a processing-transmission circuit disposed in the first unit and configured to receive the millimeter-wave carrier wave generated by the millimeter-wave carrier-wave generation circuit in the second unit through the waveguide path, generate a millimeter-wave modulated wave by superimposing the video signal generated by the image pickup device on the millimeter-wave carrier wave, and transmit the millimeter-wave modulated wave toward the waveguide path; and a demodulator disposed in the second unit and configured to receive the millimeter-wave modulated wave generated in the first unit through the waveguide path and regenerate the video signal generated by the image pickup device, wherein:

the second unit further includes a delay circuit disposed between the millimeter-wave carrier-wave generation circuit and the demodulator, and the delay circuit is set to provide, to a signal passing through the delay circuit, a delay time period equivalent to a round-trip signal transfer time period through the waveguide path.

12. The mobile body according to claim 11, wherein the mobile body comprises a plurality of the image pickup devices.

13. A video processing unit connected to a waveguide path through which a millimeter wave is transmitted, the video processing unit comprising:

a millimeter-wave carrier-wave generation circuit configured to generate a millimeter-wave carrier wave based on a predetermined reference signal and send the millimeter-wave carrier wave to the waveguide path;

a demodulator configured to receive, through the waveguide path, a millimeter-wave modulated wave generated by superimposing a video signal on the millimeter-wave carrier wave and regenerate the video signal by demodulating the millimeter-wave modulated wave; and a delay circuit disposed between the millimeter-wave carrier-wave generation circuit and the demodulator, wherein the delay circuit is set to provide, to a signal passing through the delay circuit, a delay time period equivalent to a round-trip signal transfer time period through the waveguide path.

* * * * *